United States Patent
Muse et al.

(10) Patent No.: US 11,013,901 B2
(45) Date of Patent: May 25, 2021

(54) SECUREMENT DEVICES, SYSTEMS, AND METHODS

(71) Applicant: Piper Access, LLC, Salt Lake City, UT (US)

(72) Inventors: Jay Muse, Salt Lake City, UT (US); Ryan S. VanDyke, Layton, UT (US)

(73) Assignee: Piper Access, LLC, Salt Lake City, UT (US)

(*) Notice: Subject to any disclaimer, the term of this patent is extended or adjusted under 35 U.S.C. 154(b) by 545 days.

(21) Appl. No.: 15/915,606

(22) Filed: Mar. 8, 2018

(65) Prior Publication Data
US 2018/0256870 A1    Sep. 13, 2018

Related U.S. Application Data

(60) Provisional application No. 62/584,373, filed on Nov. 10, 2017, provisional application No. 62/601,087, filed on Mar. 10, 2017.

(51) Int. Cl.
*A61M 39/02* (2006.01)
*A61B 17/34* (2006.01)

(52) U.S. Cl.
CPC ..... *A61M 39/0247* (2013.01); *A61B 17/3472* (2013.01); *A61B 2017/3492* (2013.01);
(Continued)

(58) Field of Classification Search
CPC .... A61M 2039/025; A61M 2039/0261; A61M 2039/0276; A61M 2039/0288;
(Continued)

(56) References Cited

U.S. PATENT DOCUMENTS

| | | |
|---|---|---|
| 1,436,707 A | 11/1922 | Gaschke |
| 2,317,648 A | 4/1943 | Siqveland |

(Continued)

FOREIGN PATENT DOCUMENTS

| | | |
|---|---|---|
| CA | 2207561 | 6/1997 |
| DE | 102007005963 A1 | 8/2008 |

(Continued)

OTHER PUBLICATIONS

PCT International Searching Authority, Notification of Transmittal of the International Search Report and the Written Opinion of the International Searching Authority for International Application No. PCT/US17/57270, dated Jan. 12, 2018, 12 pages.
(Continued)

*Primary Examiner* — Brandy S Lee
(74) *Attorney, Agent, or Firm* — Med Venture Management, LLC; Daniel C. Higgs

(57) ABSTRACT

An intraosseous access system can include a hub coupled to a cannula that can be introduced into a bone of a patient. The system further includes a securement device that can couple with the hub when transitioned from an open orientation to a closed orientation. The securement device includes a first segment and a second segment that are spaced apart from each other when the securement device is in the open orientation and are approximated and secured to each other when the securement device is in the closed orientation. The first segment includes a first receptacle that receives a portion of the hub therein and contacts the hub to restrain movement of the hub relative to the securement device when the securement device is coupled with the hub in the closed orientation. The first segment also includes a first arm coupled to the first receptacle, the first arm biasing the first receptacle toward the hub when the securement device is coupled with the hub in the closed orientation.

25 Claims, 30 Drawing Sheets

(52) U.S. Cl.
CPC .......... *A61M 2039/025* (2013.01); *A61M 2039/0261* (2013.01); *A61M 2039/0276* (2013.01); *A61M 2039/0288* (2013.01)

(58) Field of Classification Search
CPC ...... A61M 39/0247; A61M 2025/0681; A61M 25/1025; A61M 39/28; A61M 5/329; A61M 25/00; A61M 2025/0063; A61M 25/0097; A61M 25/0113; A61M 25/065; A61M 25/0662; A61M 5/14244; A61M 5/158; A61M 2202/0007; A61M 2005/14252; A61M 2005/1585; A61M 2039/087; A61M 25/01; A61M 39/10; A61M 5/14; A61M 2025/0006; A61M 2039/1016; A61M 2202/10; A61M 2210/02; A61B 17/3472; A61B 2017/3492
See application file for complete search history.

(56) References Cited

U.S. PATENT DOCUMENTS

| | | |
|---|---|---|
| 4,275,721 A | 6/1981 | Olson |
| 4,321,914 A | 3/1982 | Begovac et al. |
| 4,356,828 A | 11/1982 | Jamshidi |
| 4,469,109 A | 9/1984 | Mehl |
| 4,593,681 A | 6/1986 | Soni |
| 4,736,742 A | 4/1988 | Alexson et al. |
| 4,755,170 A | 7/1988 | Golden |
| 4,755,173 A | 7/1988 | Konopka et al. |
| 4,758,225 A | 7/1988 | Cox et al. |
| 4,889,529 A | 12/1989 | Haindl |
| 4,929,241 A | 5/1990 | Kulli |
| 4,944,677 A | 7/1990 | Alexandre |
| 4,952,207 A | 8/1990 | Lemieux |
| 4,964,854 A | 10/1990 | Luther |
| 4,969,870 A | 11/1990 | Kramer et al. |
| 4,978,344 A | 12/1990 | Dombrowski et al. |
| 5,040,542 A | 8/1991 | Gray |
| 5,042,558 A | 8/1991 | Hussey et al. |
| 5,049,136 A | 9/1991 | Johnson |
| 5,053,017 A | 10/1991 | Chamuel |
| 5,073,169 A | 12/1991 | Raiken |
| 5,120,321 A | 6/1992 | Oksman et al. |
| 5,122,114 A | 6/1992 | Miller et al. |
| 5,135,504 A | 8/1992 | McLees |
| 5,137,520 A | 8/1992 | Maxson et al. |
| 5,183,468 A | 2/1993 | McLees |
| 5,207,697 A | 5/1993 | Carusillo et al. |
| 5,215,528 A | 6/1993 | Purdy et al. |
| 5,263,939 A | 11/1993 | Wortrich |
| 5,271,744 A | 12/1993 | Kramer et al. |
| 5,279,591 A | 1/1994 | Simon |
| 5,300,045 A | 4/1994 | Plassche, Jr. |
| 5,304,151 A | 4/1994 | Kuracina |
| 5,312,351 A | 5/1994 | Gerrone |
| 5,312,364 A | 5/1994 | Jacobs |
| 5,322,517 A | 6/1994 | Sircom et al. |
| 5,328,482 A | 7/1994 | Sircom et al. |
| 5,332,398 A | 7/1994 | Miller et al. |
| 5,334,158 A | 8/1994 | McLees |
| 5,344,408 A | 9/1994 | Partika |
| 5,348,544 A | 9/1994 | Sweeney et al. |
| 5,354,283 A | 10/1994 | Bark et al. |
| 5,357,974 A | 10/1994 | Baldridge |
| 5,364,367 A | 11/1994 | Banks et al. |
| 5,366,446 A | 11/1994 | Tal et al. |
| 5,368,046 A | 11/1994 | Scarfone et al. |
| 5,375,588 A | 12/1994 | Yoon |
| 5,405,348 A | 4/1995 | Anspach, Jr. et al. |
| 5,423,766 A | 6/1995 | Di Cesare |
| 5,431,655 A | 7/1995 | Melker et al. |
| 5,449,370 A | 9/1995 | Vaitekunas |
| 5,451,210 A | 9/1995 | Kramer et al. |
| 5,458,658 A | 10/1995 | Sircom |
| 5,472,427 A | 12/1995 | Rammler |
| 5,533,974 A | 7/1996 | Gaba |
| 5,554,154 A | 9/1996 | Rosenberg |
| 5,556,411 A | 9/1996 | Taoda et al. |
| 5,558,651 A | 9/1996 | Crawford et al. |
| 5,562,633 A | 10/1996 | Wozencroft |
| 5,571,133 A | 11/1996 | Yoon |
| 5,584,810 A | 12/1996 | Brimhall |
| 5,591,188 A | 1/1997 | Waisman |
| 5,601,559 A | 2/1997 | Melker et al. |
| 5,662,610 A | 9/1997 | Sircom |
| 5,667,509 A | 9/1997 | Westin |
| 5,683,378 A | 11/1997 | Christy |
| 5,697,907 A | 12/1997 | Gaba |
| 5,779,708 A | 7/1998 | Wu |
| 5,807,275 A | 9/1998 | Jamshidi |
| 5,882,337 A | 3/1999 | Bogert et al. |
| 6,001,080 A | 12/1999 | Kuracina et al. |
| 6,004,294 A | 12/1999 | Brimhall et al. |
| 6,071,284 A | 6/2000 | Fox |
| 6,077,244 A | 6/2000 | Botich et al. |
| 6,117,108 A | 9/2000 | Woehr et al. |
| 6,132,401 A | 10/2000 | Van Der Meyden et al. |
| 6,135,769 A | 10/2000 | Kwan |
| 6,183,442 B1 | 2/2001 | Athanasiou et al. |
| 6,228,088 B1 | 5/2001 | Miller et al. |
| 6,247,928 B1 | 6/2001 | Meller et al. |
| 6,273,715 B1 | 8/2001 | Meller et al. |
| 6,287,278 B1 | 9/2001 | Woehr et al. |
| 6,443,927 B1 | 9/2002 | Cook |
| 6,443,929 B1 | 9/2002 | Kuracina et al. |
| 6,585,704 B2 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,626,887 B1 | 9/2003 | Wu |
| 6,629,959 B2 | 10/2003 | Kuracina et al. |
| 6,652,486 B2 | 11/2003 | Bialecki et al. |
| 6,652,490 B2 | 11/2003 | Howell |
| 6,699,242 B2 | 3/2004 | Heggeness |
| 6,749,588 B1 | 6/2004 | Howell et al. |
| 6,761,726 B1 | 7/2004 | Findlay et al. |
| 6,796,962 B2 | 9/2004 | Ferguson et al. |
| 6,814,734 B2 | 11/2004 | Chappuis et al. |
| 6,860,871 B2 | 3/2005 | Kuracina et al. |
| 6,875,219 B2 | 4/2005 | Arramon et al. |
| 6,902,546 B2 | 6/2005 | Ferguson |
| 6,984,213 B2 | 1/2006 | Horner et al. |
| 7,004,927 B2 | 2/2006 | Ferguson et al. |
| 7,008,402 B2 | 3/2006 | Ferguson et al. |
| 7,070,580 B2 | 7/2006 | Nielsen |
| 7,179,244 B2 | 2/2007 | Smith et al. |
| 7,226,434 B2 | 6/2007 | Carlyon et al. |
| 7,264,613 B2 | 9/2007 | Woehr et al. |
| 7,341,573 B2 | 3/2008 | Ferguson et al. |
| 7,354,422 B2 | 4/2008 | Riesenberger et al. |
| 7,357,784 B2 | 4/2008 | Ferguson |
| 7,413,562 B2 | 8/2008 | Ferguson et al. |
| 7,458,954 B2 | 12/2008 | Ferguson et al. |
| 7,524,306 B2 | 4/2009 | Botich et al. |
| 7,588,559 B2 | 9/2009 | Aravena et al. |
| 7,601,139 B2 | 10/2009 | Woehr et al. |
| 7,611,485 B2 | 11/2009 | Ferguson |
| 7,618,395 B2 | 11/2009 | Ferguson |
| 7,670,328 B2 | 3/2010 | Miller |
| 7,699,808 B2 | 4/2010 | Marrs et al. |
| 7,699,850 B2 | 4/2010 | Miller |
| 7,749,225 B2 | 7/2010 | Chappuis et al. |
| 7,811,260 B2 | 10/2010 | Miller et al. |
| 7,815,642 B2 | 10/2010 | Miller |
| 7,850,620 B2 | 12/2010 | Miller et al. |
| 7,935,080 B2 | 5/2011 | Howell et al. |
| 7,967,792 B2 | 6/2011 | Bierman |
| 7,972,339 B2 | 7/2011 | Nassiri et al. |
| 8,038,664 B2 | 10/2011 | Miller et al. |
| 8,043,229 B2 | 10/2011 | Mulvihill et al. |
| 8,096,973 B2 | 1/2012 | Snow et al. |
| 8,142,365 B2 | 3/2012 | Miller |

(56) References Cited

U.S. PATENT DOCUMENTS

| | | |
|---|---|---|
| 8,206,355 B2 | 6/2012 | Thorne |
| 8,211,070 B2 | 7/2012 | Woehr et al. |
| 8,246,584 B2 | 8/2012 | Aravena et al. |
| 8,486,024 B2 | 7/2013 | Steube |
| 8,506,568 B2 | 8/2013 | Miller |
| 8,591,467 B2 | 11/2013 | Walker et al. |
| 8,628,497 B2 | 1/2014 | Finnestad et al. |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,715,287 B2 | 5/2014 | Miller |
| 8,844,112 B2 | 9/2014 | Snow et al. |
| 8,845,584 B2 | 9/2014 | Ferguson et al. |
| 8,864,714 B2 | 10/2014 | Harding et al. |
| 8,876,826 B2 | 11/2014 | Miller |
| 8,926,563 B2 | 1/2015 | Steube |
| 8,944,069 B2 | 2/2015 | Miller et al. |
| 8,974,410 B2 | 3/2015 | Miller et al. |
| 8,992,535 B2 | 3/2015 | Miller |
| 9,072,543 B2 | 7/2015 | Miller et al. |
| 9,220,483 B2 | 12/2015 | Frankhouser et al. |
| 9,295,487 B2 | 3/2016 | Miller et al. |
| 9,314,228 B2 | 4/2016 | Miller |
| 9,314,270 B2 | 4/2016 | Miller |
| 9,393,031 B2 | 7/2016 | Miller |
| 9,399,119 B2 | 7/2016 | Kuracina et al. |
| 9,408,632 B2 | 8/2016 | Erskine |
| 9,414,815 B2 | 8/2016 | Miller et al. |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,539,398 B2 | 1/2017 | Ferguson et al. |
| 9,545,243 B2 | 1/2017 | Miller et al. |
| 9,889,255 B2 | 2/2018 | Sonderegger et al. |
| 2001/0011164 A1 | 8/2001 | Bierman |
| 2002/0123724 A1 | 9/2002 | Douglas et al. |
| 2003/0225344 A1 | 12/2003 | Miller |
| 2003/0225411 A1 | 12/2003 | Miller |
| 2004/0059317 A1 | 3/2004 | Hermann |
| 2004/0220497 A1 | 11/2004 | Findlay et al. |
| 2005/0027263 A1 | 2/2005 | Woehr et al. |
| 2005/0033235 A1 | 2/2005 | Flint |
| 2005/0101933 A1 | 5/2005 | Marrs et al. |
| 2005/0107743 A1 | 5/2005 | Fangrow, Jr. |
| 2005/0165404 A1 | 7/2005 | Miller |
| 2005/0245878 A1 | 11/2005 | Mernoe et al. |
| 2006/0015066 A1 | 1/2006 | Turieo et al. |
| 2006/0025723 A1 | 2/2006 | Ballarini |
| 2006/0106402 A1 | 5/2006 | McLucas |
| 2007/0049945 A1 | 3/2007 | Miller |
| 2007/0270775 A1 | 11/2007 | Miller et al. |
| 2008/0140014 A1* | 6/2008 | Miller ............... A61M 39/0247 604/180 |
| 2008/0215056 A1 | 9/2008 | Miller et al. |
| 2008/0221580 A1 | 9/2008 | Miller et al. |
| 2009/0054808 A1 | 2/2009 | Miller |
| 2009/0093830 A1 | 4/2009 | Miller |
| 2009/0118639 A1 | 5/2009 | Moos et al. |
| 2009/0204024 A1 | 8/2009 | Miller |
| 2009/0306697 A1 | 12/2009 | Fischvogt |
| 2010/0152616 A1 | 6/2010 | Beyhan et al. |
| 2010/0298784 A1 | 11/2010 | Miller |
| 2011/0028976 A1 | 2/2011 | Miller |
| 2011/0082387 A1 | 4/2011 | Miller et al. |
| 2013/0030370 A1 | 1/2013 | Walker et al. |
| 2013/0096561 A1 | 4/2013 | Miller et al. |
| 2014/0100528 A1 | 4/2014 | Finnestad et al. |
| 2014/0142577 A1 | 5/2014 | Miller |
| 2014/0276471 A1 | 9/2014 | Emery et al. |
| 2014/0277028 A1 | 9/2014 | Voic |
| 2014/0343454 A1 | 11/2014 | Miller et al. |
| 2015/0127006 A1 | 5/2015 | Miller |
| 2015/0230823 A1 | 8/2015 | Morgan et al. |
| 2015/0231364 A1 | 8/2015 | Blanchard et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0183974 A1 | 6/2016 | Miller |
| 2016/0184509 A1 | 6/2016 | Miller et al. |
| 2016/0206346 A1 | 7/2016 | Miller |
| 2017/0007271 A1 | 1/2017 | Miller et al. |
| 2017/0311981 A1 | 11/2017 | Real et al. |
| 2018/0125465 A1 | 5/2018 | Muse et al. |
| 2018/0256209 A1 | 9/2018 | Muse et al. |
| 2018/0256870 A1 | 9/2018 | Muse et al. |
| 2019/0282244 A1 | 9/2019 | Muse |

FOREIGN PATENT DOCUMENTS

| | | |
|---|---|---|
| EP | 0548612 A1 | 6/1993 |
| EP | 2849656 B1 | 5/2013 |
| EP | 2967508 B1 | 1/2016 |
| FR | 2481930 | 11/1981 |
| FR | 2522973 A2 | 9/1983 |
| FR | 2885512 A1 | 11/2006 |
| JP | 2000140125 A | 12/1998 |
| NL | 9401085 A | 6/1994 |
| WO | 200213893 A1 | 2/2002 |
| WO | 2008065646 A1 | 6/2008 |
| WO | 2013173360 A1 | 11/2013 |
| WO | 2014144239 A1 | 9/2014 |
| WO | 2018075694 A1 | 4/2018 |
| WO | 20180165334 A1 | 9/2018 |
| WO | 20180165339 A1 | 9/2018 |
| WO | 20190164990 A1 | 8/2019 |

OTHER PUBLICATIONS

Prometheus Medical Ltd., Prometheus PIN, Undated, Downloaded from https://www.prometheusmedical.co.uk/equipment/prometheus-equipment-intraosseous-access/prometheus-pin on Aug. 10, 2017, 2 pages.

United States Patent and Trademark Office, Office Action in U.S. Appl. No. 15/787,671, dated Feb. 27, 2020, 12 pages.

United States Patent and Trademark Office, Notice of Allowance in U.S. Appl. No. 15/787,671, dated Sep. 16, 2020, 18 pages.

United States Patent and Trademark Office, Notice of Allowance in U.S. Appl. No. 15/787,671, dated Dec. 31, 2020, 53 pages.

United States Patent and Trademark Office, Office Action in U.S. Appl. No. 15/914,964, dated Aug. 21, 2020, 19 pages.

U.S. Appl. No. 15/787,671, filed Oct. 18, 2017, Intraosseous Access Devices, Systems, and Methods.

U.S. Appl. No. 15/914,964, filed Mar. 7, 2018, Safety Shields for Elongated Instruments and Related Systems and Methods.

U.S. Appl. No. 16/280,897, filed Feb. 20, 2019, Medical Drilling Devices and Related Systems and Methods.

* cited by examiner

SECUREMENT DEVICES, SYSTEMS, AND METHODS

CROSS-REFERENCE TO RELATED APPLICATIONS

This application claims the benefit under 35 U.S.C. § 119(e) of U.S. Provisional Patent Application No. 62/601,087, titled HUB SECUREMENT SYSTEM, filed on Mar. 10, 2017, and U.S. Provisional Patent Application No. 62/584,373, titled SECUREMENT DEVICES, SYSTEMS, AND METHODS, filed on Nov. 10, 2017, the entire contents of each of which are hereby incorporated by reference herein.

TECHNICAL FIELD

Certain embodiments described herein relate generally to securement devices for attaching medical apparatus to a patient, and further embodiments relate more particularly to securement devices for intraosseous access apparatus.

BACKGROUND

Various devices, systems, and methods have been developed to secure medical apparatus, such as vascular access devices, to a patient after those instruments have been introduced into the patient. Such devices, systems, and methods can prevent the medical apparatus from being inadvertently removed from the patient. Known devices, systems, and methods, however, suffer from one or more drawbacks that can be resolved, remedied, ameliorated, or avoided by certain embodiments described herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
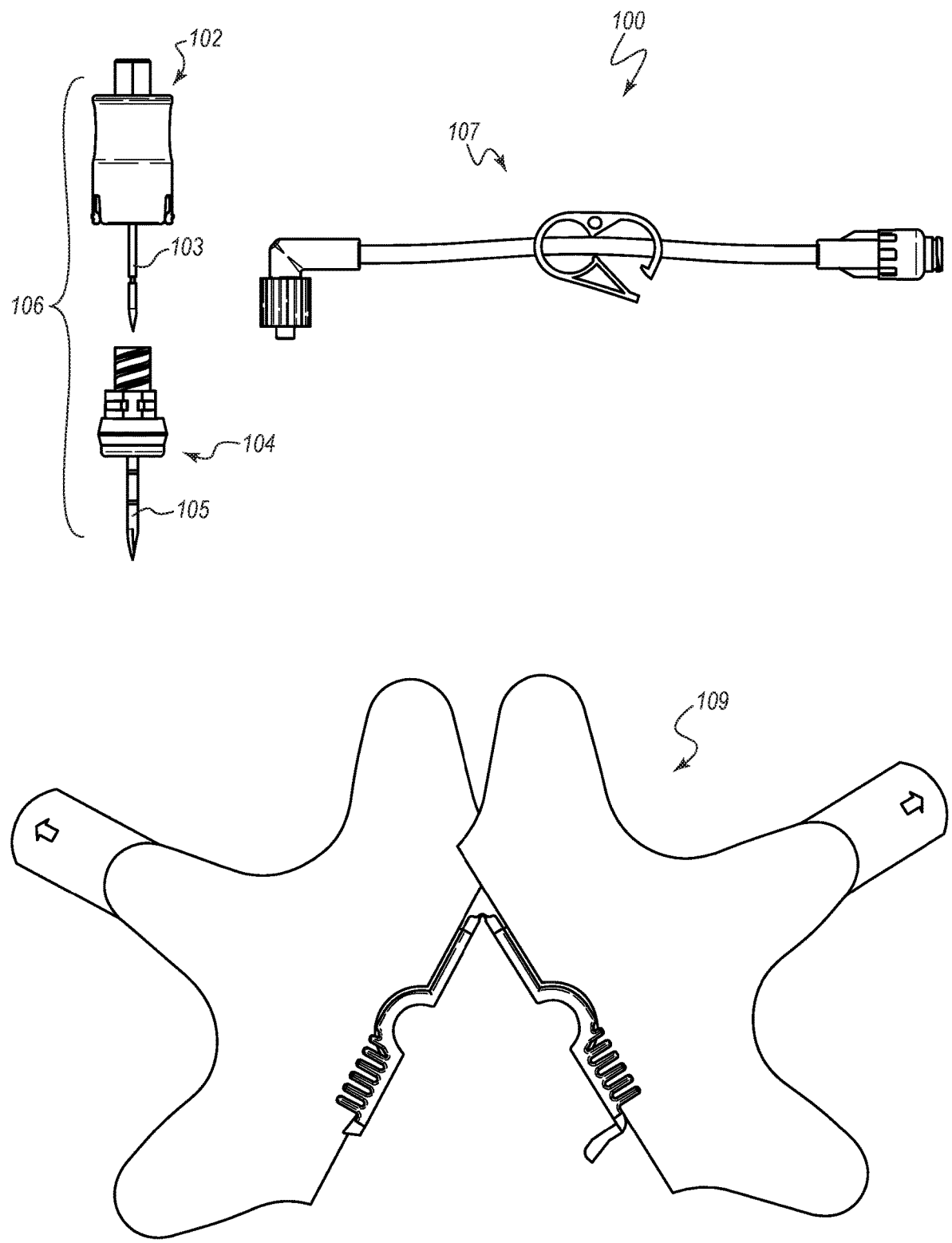
FIG. 1 depicts an embodiment of an intraosseous access system, with some of the components shown in side elevation views and another component shown in a top plan view.

The present disclosure relates generally to securement devices, systems, and methods for attaching medical instruments to a patient, and relates more particularly to securement devices for intraosseous access apparatus. For purposes of illustration, much of the disclosure herein pertains to devices for securing a conduit or communication passageway to a patient and/or stabilizing the conduit relative to the patient after the conduit has been introduced into an interior of a bone structure of the patient, such as by drilling through or otherwise penetrating hard, compact bone tissue to gain access to soft bone marrow. Once access to the soft bone marrow is achieved, any of a variety of suitable procedures can be performed, such as, for example, infusion, aspiration, or extraction of bone marrow or other components of the bone. Numerous situations can benefit from providing access to bone marrow in this manner, such as, for example, when other methods of accessing a vein with an IV needle are difficult or in emergency situations, such as heart attack, burns, drug overdoses, etc., when rapid access to the marrow may be desired.

Certain embodiments of securement devices and systems disclosed herein can be particularly advantageous in emergency situations. For example, in some instances, it can be desirable to introduce a cannula into a bone of a patient such that a proximally located cannula hub is at an exterior of the patient, and then communicate as soon as possible thereafter with the interior of the bone via the cannula. In further instances, a connector of any suitable variety, such as may be included with an extension assembly, is coupled with the cannula hub in establishing the communication with the interior of the bone. Some embodiments permit such coupling to occur prior to the securement device being coupled to the cannula hub. In this manner, fluid communication with the bone can be established quickly, and without delays that might otherwise arise from attaching the securement device to the cannula hub.

Other or further advantages may also be achieved by securement devices and systems disclosed herein. For example, some embodiments permit the extension assembly or other connector element to remain coupled with the cannula hub during attachment of the securement device to the cannula hub, which can facilitate the attachment procedure. For example, unlike some known devices, such embodiments may not require removal of the connector or extension assembly from the cannula hub in order to attach the securement device to the cannula hub. Accordingly, fewer steps for connection can be required and/or a risk of accidental contact with the cannula hub (e.g., which could contaminate the cannula hub and/or loosen or dislodge the cannula) can be reduced. Stated otherwise, the securement device can be secured to the cannula hub without first removing an extension assembly or other connector from the cannula hub.

Some embodiments define a low profile, which can, for example, reduce the likelihood of inadvertent contact with the securement device and/or the cannula hub (e.g., which contact could lead to contamination or possible dislodgement of the cannula). In some embodiments, a maximum lateral perimeter of the cannula hub extends only a short distance from a longitudinal axis of the hub. For example, in some embodiments, the cannula hub may be devoid of an outwardly extending flange and the securement device can be secured directly to a body of the hub. In some instances, the securement device can directly contact the portion of the hub that defines the maximum lateral perimeter and can be in close proximity thereto, which can contribute to the low profile of the assembled system.

Some embodiments can allow for any of a variety of different axial orientations between the cannula hub and the securement device. The securement device thus can accommodate a variety of orientations of the cannula hub relative to the skin of the patient at the point of insertion of the cannula.

One or more of the foregoing advantages of various embodiments disclosed herein will be apparent from the discussion that follows. Other or further advantages will also be apparent.

FIG. 1 depicts an embodiment of an intraosseous access system 100, with several components thereof shown in side elevation views and another component thereof shown in a top elevation view. The illustrated system 100 includes an obturator assembly 102 and a needle assembly 104, which together may be referred to as an access assembly 106 or as an access system 106.

As further discussed below, in the illustrated embodiment, the obturator assembly 102 includes an obturator 103. However, in various other embodiments, the obturator 103 may be replaced with a different elongated medical instrument, such as, for example, a trocar, a needle, or a stylet, and/or may be referred to by a different name, such as one or more of the foregoing examples. Accordingly, the obturator assembly 102 may be referred to more generally as an elongated medical instrument assembly. In like manner, the obturator 103 may be referred to more generally as an elongated medical instrument.

Similarly, the needle assembly 104 is referred to as such herein for convenience. In the illustrated embodiment, the needle assembly 104 includes a needle 105. However, in various other embodiments, the needle 105 may be replaced with a different instrument, such as, for example, a cannula, a tube, or a sheath, and/or may be referred to by a different name, such as one or more of the foregoing examples. Accordingly, the needle assembly 104 may be referred to more generally as a cannula assembly or as a tube assembly. In like manner, the needle 105 may be referred to more generally as a cannula.

As further discussed below, the obturator assembly 102 and the needle assembly 104 can be selectively coupled together and introduced into a bone of a patient. With the access system 106 thus assembled, any suitable driver (not shown) may be used to introduce the needle 105 into the bone. For example, the driver may include a handle that is manually operable by a user or may include a powered driver of any suitable variety (e.g., an electrical drill).

In some embodiments, the intraosseous access system 100 can further include an extension set or extension assembly 107. As further discussed below, the extension assembly 107 can be configured to couple with the needle assembly 104 after it has been introduced into the bone of the patient. The extension assembly 107 can serve as an intermediary for coupling other medical devices to the needle assembly 104.

In other or further embodiments, the intraosseous access system 100 can include a securement assembly or securement device 109 that is configured to couple with the needle assembly 104. For example, the securement device 109 can be coupled with the needle assembly 104 after the needle assembly 104 has been introduced into the bone of the patient and/or after the extension assembly 107 (if present) has been attached to the needle assembly 104. In other or further instances, the securement device 109 can be coupled with the needle assembly 104 prior to coupling the extension assembly 107 with the needle assembly 104. The securement device 109 can be configured to secure the needle assembly 104 to the patient and/or stabilize the needle assembly 104 relative to the patient.

Figure 2:
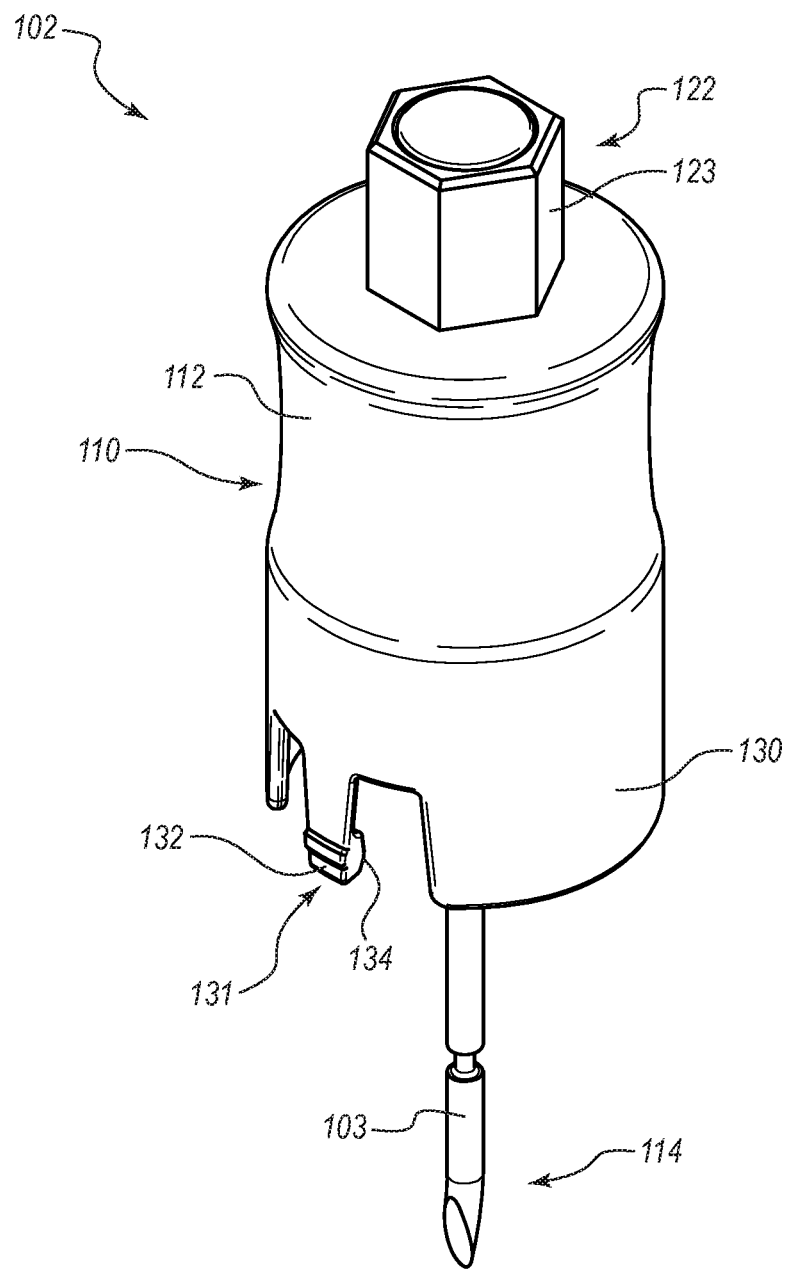
FIG. 2 is a perspective view of an embodiment of an obturator assembly that is compatible with the intraosseous access system of FIG. 1.
Figure 3:
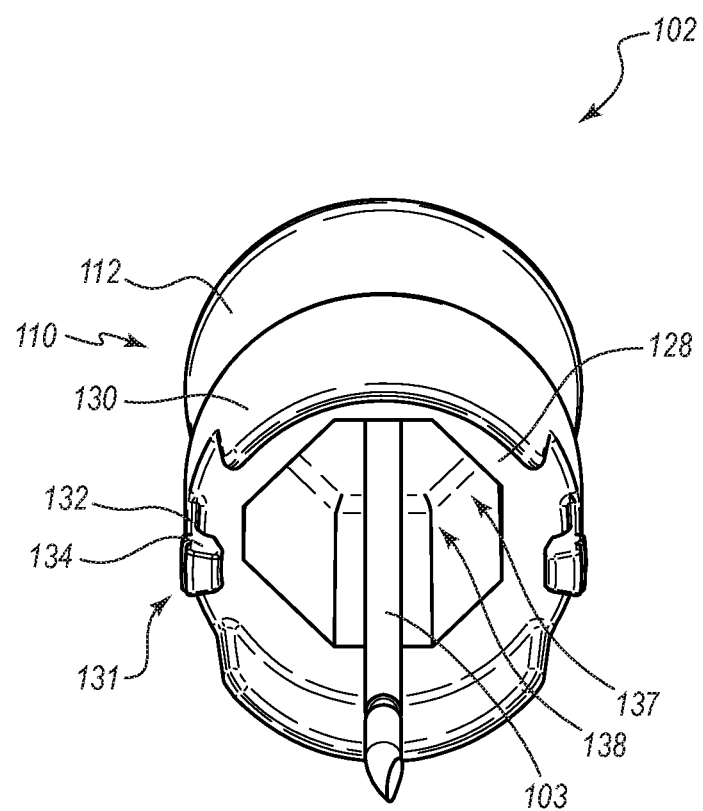
FIG. 3 is another perspective view of the obturator assembly.

With reference to FIGS. 2 and 3, the obturator assembly 102 can include a coupling hub 110 that is attached to the obturator 103 in any suitable manner. The coupling hub 110 can be configured to interface with any suitable driver 101, as previously mentioned. The coupling hub 110 may alternatively be referred to as an obturator hub 110 or, more generally, as an elongated instrument hub 110.

In the illustrated embodiment, the obturator hub 110 includes a body or housing 112. A proximal end of the housing 112 can be coupled with (e.g., may be attached to or may itself define) a coupling interface 122 for coupling with a complementary or otherwise suitable coupling interface of a driver. In the illustrated embodiment, the coupling interface 122 is formed as a shaft 123 that is configured to be received within a driver socket. For example, the shaft 123 can interface with the socket so as to be rotated thereby. Any other suitable coupling interface is contemplated. For example, the coupling interface 122 may instead be formed as a socket.

The illustrated coupling hub 110 includes a skirt 130 that extends distally from a central portion of the housing 112. The skirt 130 can include one or more mechanical coupling members 131 that are configured to selectively couple the coupling hub 110 to the needle assembly 104. In the illustrated embodiment, the skirt 130 includes two such mechanical coupling members 131 at opposite sides thereof. In particular, the illustrated embodiment includes two resilient arms or projections 132 that are capable of resiliently deforming in a lateral or radial direction. Each arm can include a snap interface, inward protrusion, or catch 134 at an internal side thereof that can interface with the needle assembly 104 to achieve the coupling configuration.

With reference to FIG. 3, the housing 112 can further define a coupling interface 137 configured to couple the coupling hub 110 to the needle assembly 104 in a manner that causes the coupling hub 110 to rotate in unison with the needle assembly 104. In the illustrated embodiment, the coupling interface 137 is formed as a socket 138 into which a shaft portion of the needle assembly 104 can be received. The socket 138 can define a keyed shape that permits the coupling hub 110 to be coupled to the needle assembly 104 in only one unique rotational or angular orientation. In particular, in the illustrated embodiment, the socket 138 defines an elongated right octagonal prism of which five contiguous sides are substantially identically sized, two enlarged sides that extend from the ends of the five contiguous sides are lengthened relative to the five contiguous sides, and an eighth shorted side that extends between the two enlarged sides is shorter than the five contiguous sides. Any other suitable keying configuration is contemplated. As further discussed below, a keyed interface such as just described can ensure that the obturator 103 and the needle 105 are coupled to each other in a manner that may be desired, in some embodiments, such as to ensure that distal faces of both components are substantially parallel to each other and/or to ensure that a distal face of the obturator 103 is fully recessed relative to a distal face of the needle 105.

Figure 4:
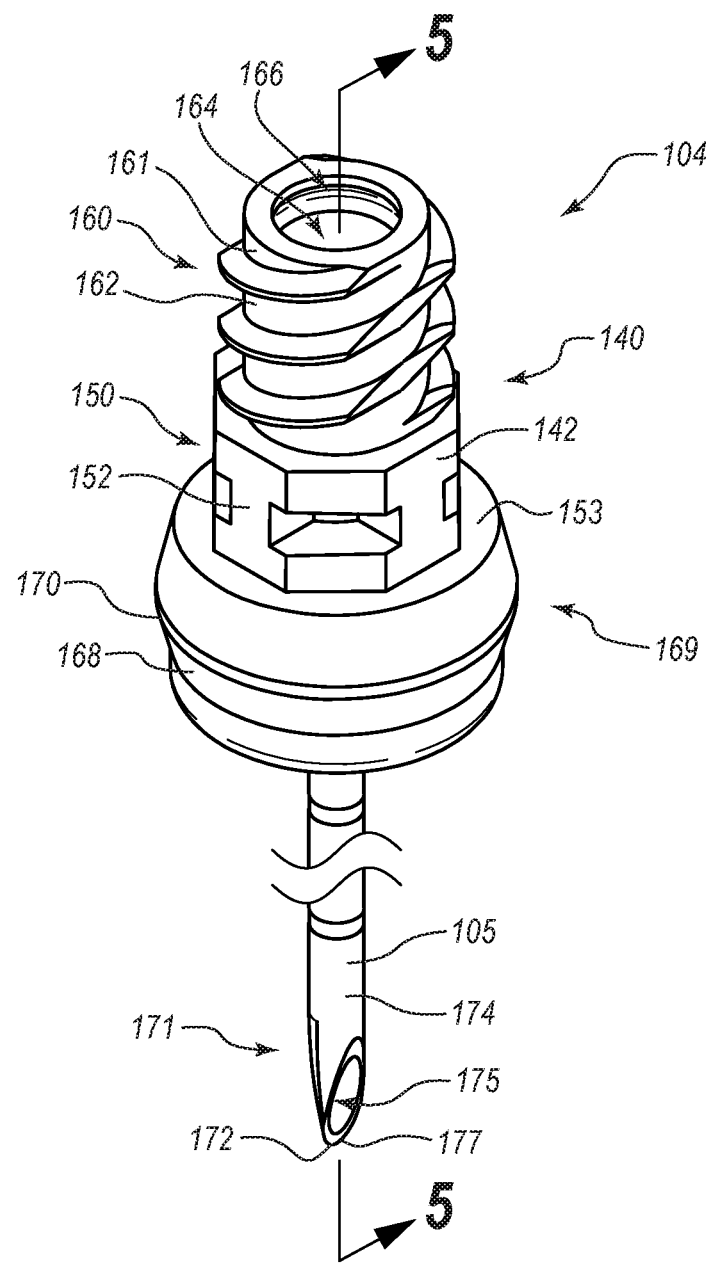
FIG. 4 is a perspective view of an embodiment of a cannula assembly that is compatible with the intraosseous access system of FIG. 1.
Figure 5:
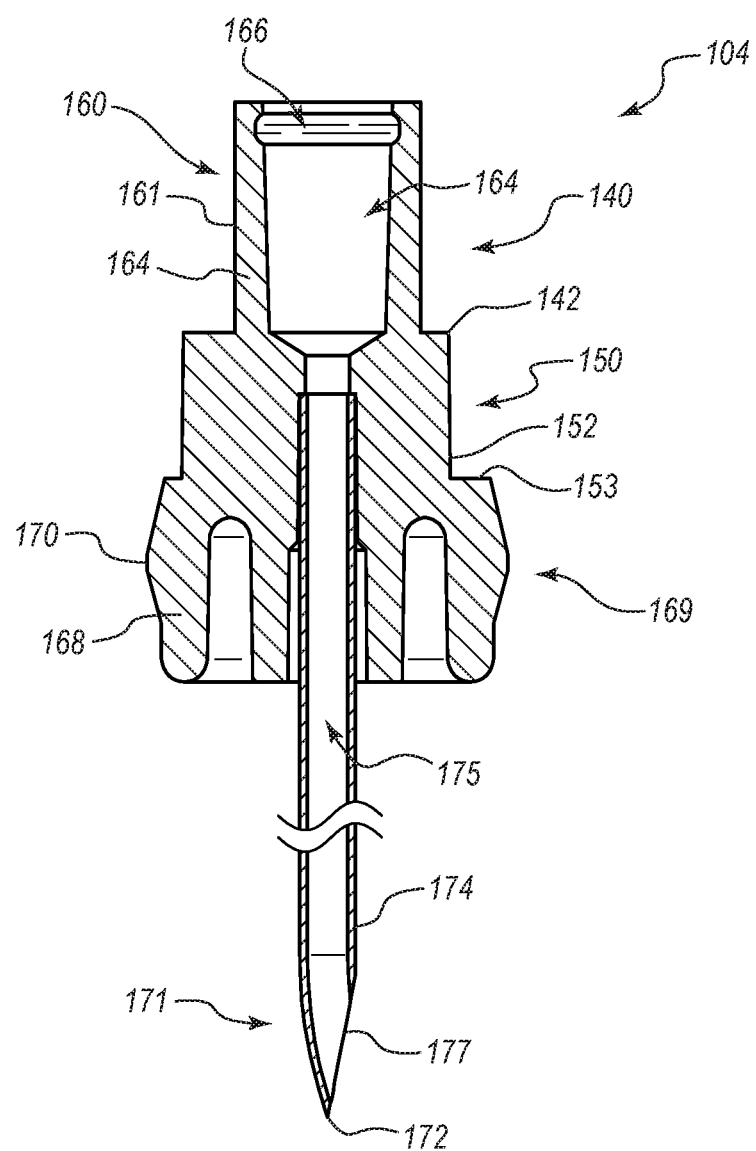
FIG. 5 is a cross-sectional view of the cannula assembly taken along the view line 5-5 in FIG. 4.

With reference to FIGS. 4 and 5, the needle assembly 104 can include a needle hub 140 that is attached to the needle 105 in any suitable manner. The needle hub 140 can be configured to couple with the coupling hub 110 and may thereby be coupled with a driver. The needle hub 140 may alternatively be referred to as a cannula hub 140.

In the illustrated embodiment, the needle hub 140 includes a housing or body 142 that is coupled to the needle 105. The body 142 can define a coupling interface 150 that is configured to couple with the coupling interface 137 of the coupling hub 102 (see FIG. 3). For example, the coupling interface 150 can be formed as a shaft 152 that is configured to be received within the socket 138 of the coupling hub 102. In some embodiments, the shaft 152 can define a keyed shape that permits the needle hub 140 to be coupled to the coupling hub 110 in only one unique rotational or angular orientation. In particular, in the illustrated embodiment, the shaft 152 defines an elongated right octagonal prism of which five contiguous sides are substantially identically sized, two enlarged sides that extend from the ends of the five contiguous sides are lengthened relative to the five contiguous sides, and an eighth shorted side that extends between the two enlarged sides is shorter than the five contiguous sides, and thus may be substantially complementary to the configuration of the socket 138. Any other suitable keying configuration is contemplated. In the illustrated embodiment, the shaft 152 extends proximally from a shoulder region 153 of the body 142.

The needle hub 140 can further include a connector 160, e.g., a medical connector, of any suitable variety. The connector 160 may be defined by the housing 142 and may extend proximally from the shaft 152. The connector 160 can be configured to couple with any suitable medical equipment, such as for infusing fluid into a patient, after the needle 105 has been inserted into bone. For example, in the illustrated embodiment, the connector 160 is formed as a Luer fitting 161 (i.e., a female Luer fitting). The illustrated Luer fitting 161 includes a sidewall 162 that defines a cavity or lumen 164. In some embodiments, a portion of a male Luer fitting may be received within the lumen 164 when the needle hub 140 is in use. The lumen 164 of the connector 160 can be in fluid communication with a lumen 175 of the needle 105, which is discussed further below.

Figure 14A:
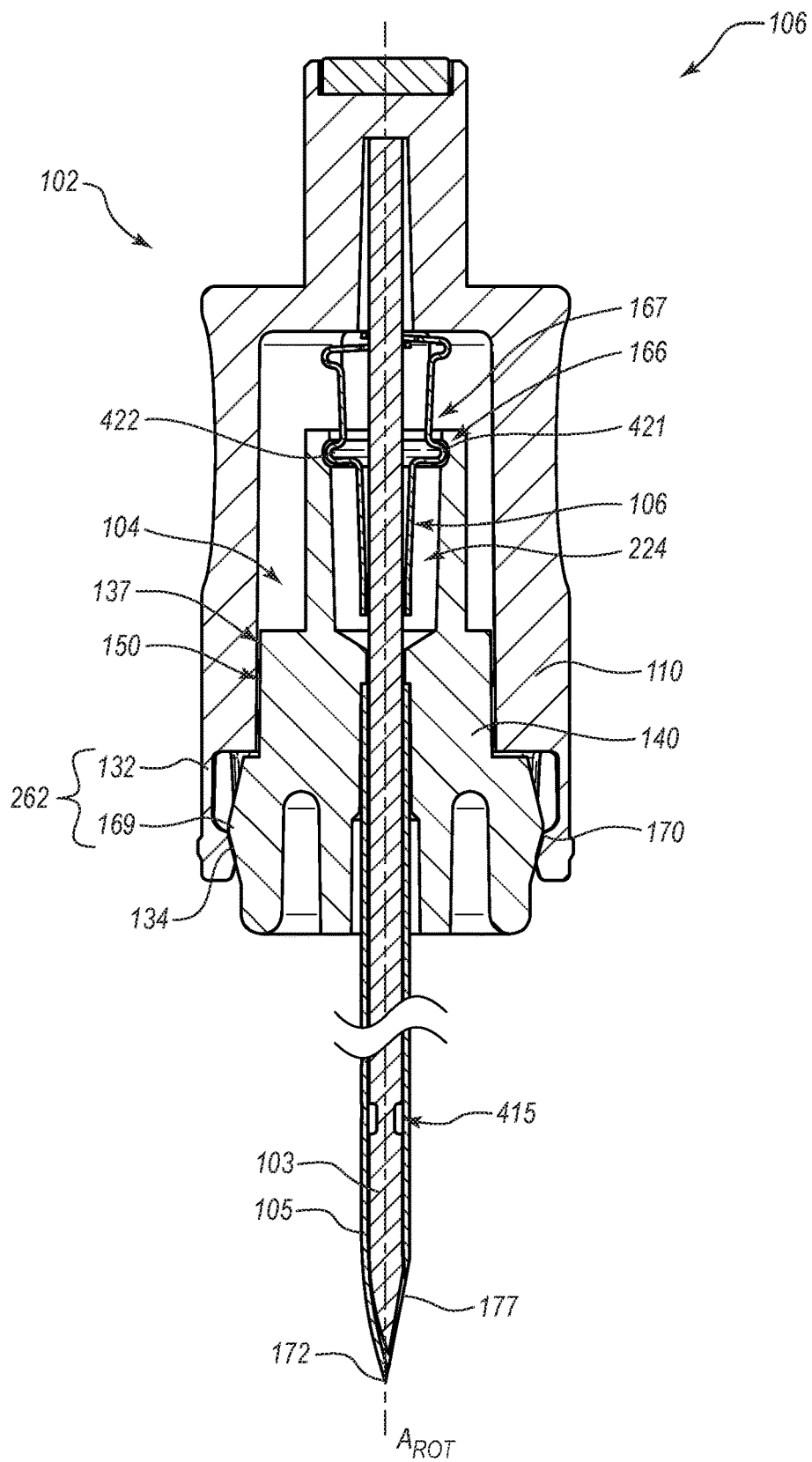
FIG. 14A is a cross-sectional view of the obturator assembly coupled with the cannula assembly in an early stage of an illustrative method of using the intraosseous access system.
Figure 14B:
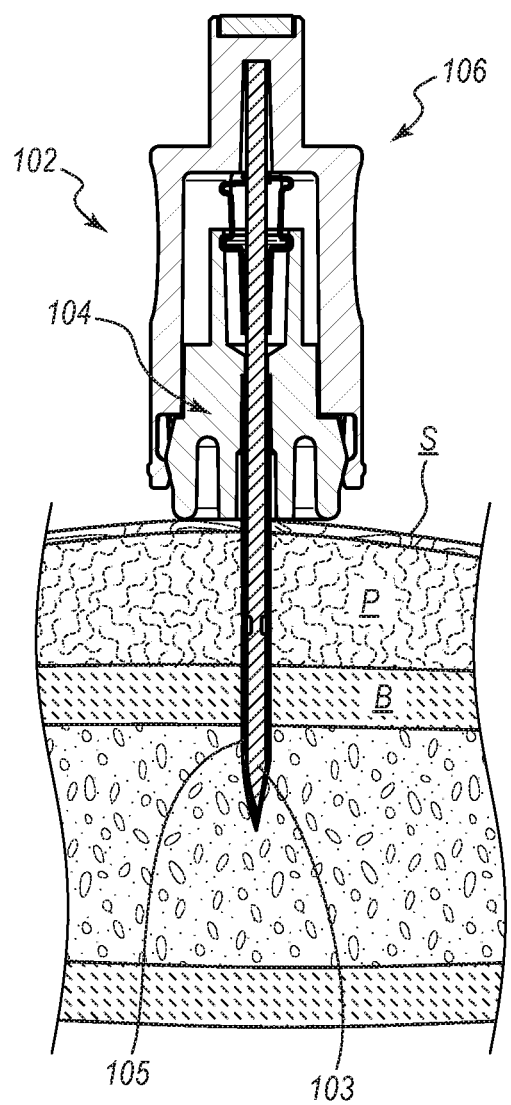
FIG. 14B is a cross-sectional view of the obturator assembly coupled with the cannula assembly in a later stage of the illustrative method in which the coupled assemblies have been inserted into a bone of a patient.

In the illustrated embodiment, the sidewall 162 defines a connection interface 166 that is configured to selectively couple the needle hub 140 with a safety shield 167 (see FIGS. 14A and 14B). For example, in the illustrated embodiment, the connection interface 166 is formed as an annular groove within which the outward protrusions of the safety shield 167 can be received. Further details of embodiments of the safety shield 167 are provided in co-pending U.S. patent application Ser. No. 15/914,964, filed Mar. 7, 2018, the entire contents of each of which are hereby incorporated by reference herein.

The housing 142 may further define a skirt 168, which may extend distally from the shaft 152. The skirt 168 may also extend outwardly relative to the shaft 152. The skirt 168 may include a coupling region 169 to which the securement device 109 can be secured. In the illustrated embodiment, the coupling region 169 extends about a full perimeter of the illustrated embodiment. The coupling region 169 can be spaced from each of a proximal end and a distal end of the needle hub 140. In the illustrated embodiment, the coupling region 169 is shaped substantially as a convex or outwardly bowed region, which may be substantially bulbous. The coupling region 169 may define a ring or apex 170 at a maximum lateral extent thereof. The apex 170 may also be referred to as a maximum transverse perimeter of the hub 140. In the illustrated embodiment, the maximum transverse perimeter 170 is substantially circular, although a variety of other shapes or contours are contemplated. The maximum transverse perimeter 170 represents an outline of the needle assembly 104 when the assembly 104 is viewed from above or below, or stated otherwise, is viewed along a longitudinal axis of the needle assembly 104.

As further discussed below, in some embodiments, the securement device 109 (see FIG. 1) can be secured to the coupling region 169 in any of a variety of different angular configurations. In further embodiments, the securement device 109 may contact the maximum transverse perimeter 170 in any of the angular configurations. In some embodiments, the coupling region 169 is relatively narrow or constricted, or stated otherwise, defines a low profile. For example, in various embodiments, a diameter (e.g., a maximum transverse width) of the maximum transverse perimeter 170 is no more than about 1.5, 2.0, 2.5, 3.0, 3.5, or 4.0 times greater than a maximum inner diameter of the lumen 164.

With reference to FIG. 5, the needle 105 can include shaft 174 that defines the lumen 175. The shaft 174 includes a proximal end that is coupled to the hub 140 in any suitable manner. The shaft 174 of the needle 105 further includes a distal end 171 that terminates at a distal tip 172. The distal end 171 can further define a distal face 177, which may be beveled in any suitable manner. In some embodiments, the distal face 177 is configured to efficiently cut bone material, as further discussed in co-pending U.S. patent application Ser. No. 15/787,671, filed Oct. 18, 2017, the entire contents of which are hereby incorporated by reference herein.

As further discussed below with respect to FIGS. 14A-14D, the obturator assembly 102 can be coupled with the needle assembly 104. In this coupled state, the obturator assembly 102 and the needle assembly 104 can be introduced (e.g., drilled) into a bone of a patient. The obturator assembly 102 can then be removed from the needle assembly 104 while a distal tip of the needle assembly 104 remains in the bone of the patient. The needle assembly 104 can then be coupled with the extension assembly 107, or with any other suitable medical device, such as for purposes of fluid aspiration or infusion.

Figure 6:
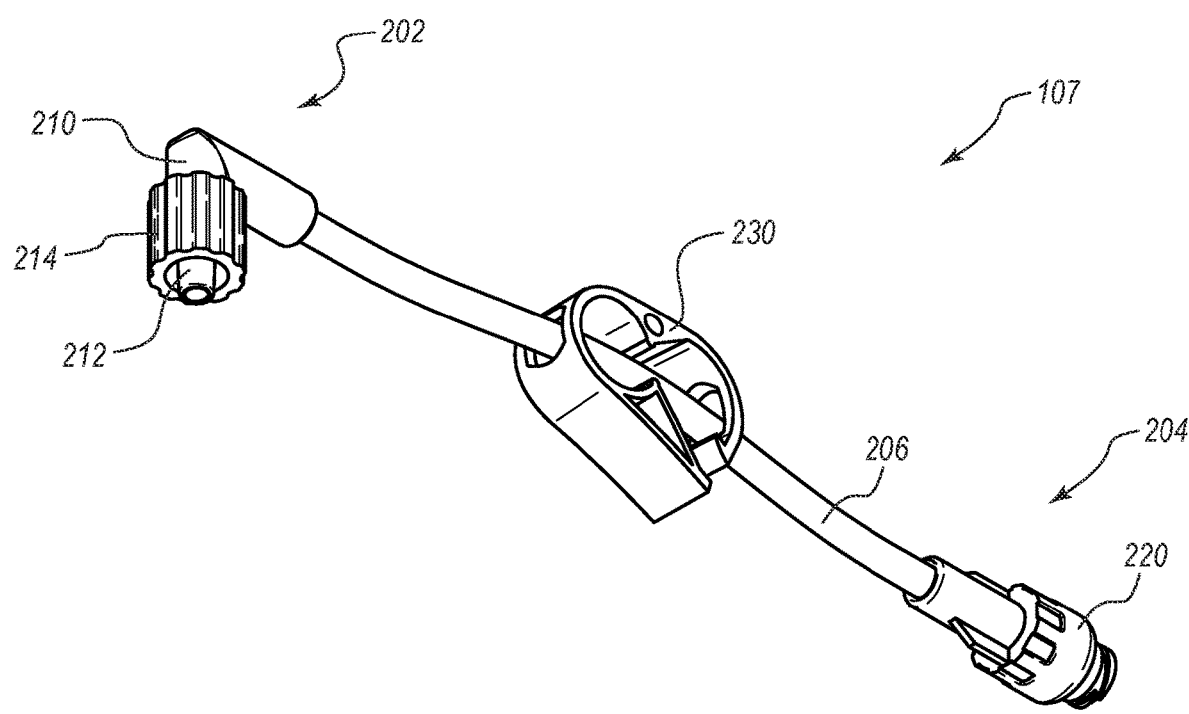
FIG. 6 is a perspective view of an embodiment of an extension assembly that is compatible with the intraosseous access system of FIG. 1.

With reference to FIG. 6, an illustrative embodiment of the extension assembly 107 can include a distal connector 202 that can selectively couple with the connector 160 of the needle hub 140. The extension assembly 107 can further include a proximal connector 204 that can be coupled with any suitable medical device, such as a medical device for achieving fluid aspiration or infusion via the needle assembly 104. The distal and proximal connectors 202, 204 can be in fluid communication with each other via any suitable conduit member, such as a length of flexible tubing 206, which may also be referred to as a tube.

A length and/or flexibility of the tubing 206 can inhibit disruption of the needle hub 140 and the insertion site of the needle 105. For example, the needle hub 140 can be less prone to movement that results from movement of a medical device when the medical device is indirectly coupled to the needle hub 140 via the extension assembly 107, rather than directly coupled to the connector 160 of the needle hub 140 (see FIGS. 4 and 5). The tubing 206 can provide physical spacing between the proximal and distal connectors 204, 202, and hence between the medical device and the needle hub 140. The flexibility of the tubing 206 can permit a range of movement between the proximal and distal connectors 204, 202, and hence between the medical device and the needle hub 140.

In the illustrated embodiment, the distal connector 202 is a two-piece luer lock connector 210 that includes a male luer 212 and a threaded collar 214. The proximal connector 204 is a female luer 220. Thus, rather than being connected directly to the female luer connector 160 of the needle hub 140, a medical device can instead be connected to the female luer connector 204.

In some embodiments, the extension assembly 107 can include a clamp 230. The clamp 230 may be of any suitable variety, and may selectively close a lumen of the flexible tubing 206 to selectively cut off fluid communication between the distal and proximal connectors 202, 204.

Figure 7:
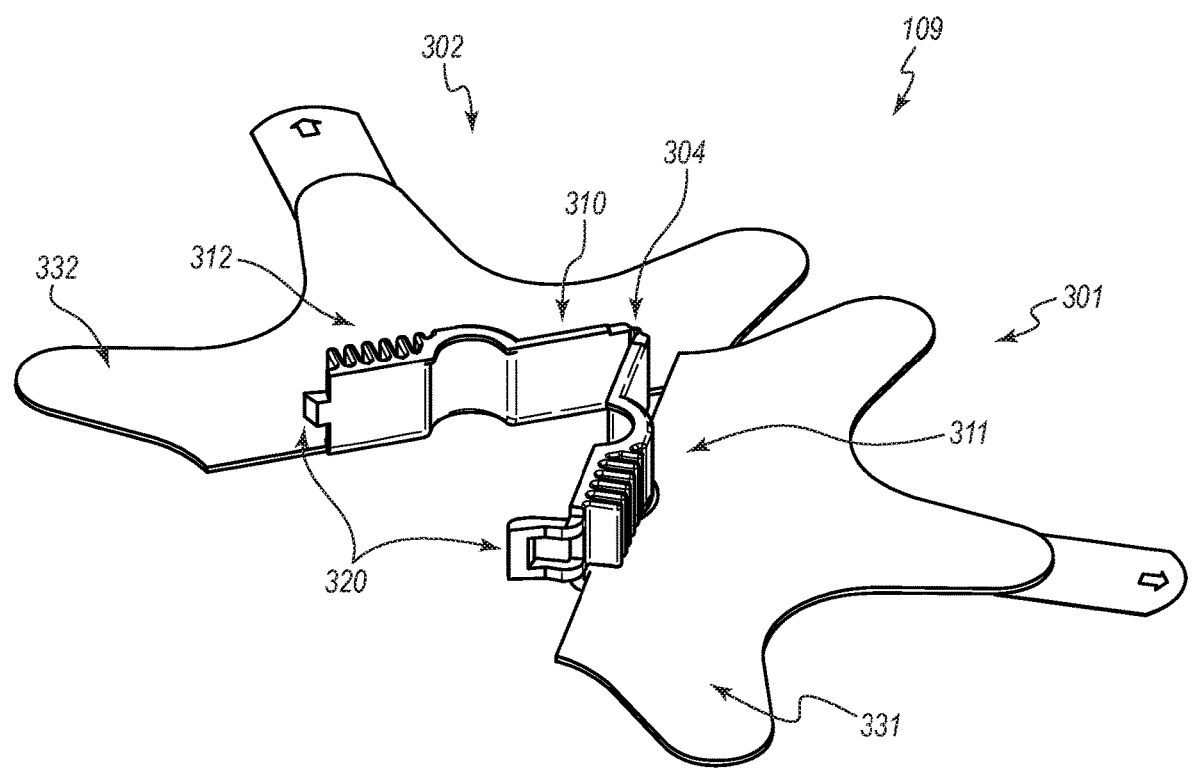
FIG. 7 is a perspective view of an embodiment of a securement device that is compatible with the intraosseous access system of FIG. 1 and that is depicted in an open orientation.

FIG. 7 is a perspective view of the securement device 109 in an open orientation. The securement device 109 can include a first segment 301 and a second segment 302 that are moveable relative to each other when the securement device 109 is in the open orientation. In the illustrated embodiment, the first and second segments 301, 302 are joined to each other at a hinge 304. Stated otherwise, the first and second segments 301, 302 are configured to rotate relative to each other about the hinge 304.

In the illustrated embodiment, the securement device 109 includes a housing, clip, or clamp 310 that defines a first branch 311 and a second branch 312. The first and second branches 311, 312 are joined to each other via the hinge 304. In some embodiments, the hinge 304 is a living hinge. For example, in some embodiments, the first and second branches 311, 312 and the hinge 304 are unitarily formed of a single piece of material (e.g., any suitable variety of plastic), and the hinge 304 is integral to the clamp 310. The clamp 310 can further define a locking mechanism or lock 320, which can be positioned opposite the hinge 304. The lock 320 can selectively secure the first and second branches 311, 312 into a fixed relation relative to each other. The securement device 109 can be said to be in a closed orientation when the first and second branches 311, 312 are secured relative to each other in such a manner.

The securement device 109 can include one or more adhesive dressings 331, 332. In the illustrated embodiment, the securement device 109 includes two separate adhesive dressings 331, 332 that are capable of moving freely relative to each other when the securement device 109 is in the open configuration. The adhesive dressings 331, 332 can be attached to the first and second branches 311, 312 of the clamp 310, respectively, and may move in unison therewith.

In some embodiments, at least a portion of one of the adhesive dressings 331, 332 can overlap the other when the securement device 109 is in the open orientation. For example, in FIG. 7, a corner of the first adhesive dressing 331 overlaps a corner of the second adhesive dressing 332 when the securement device 109 is in the open orientation. Overlapping of one adhesive dressing relative to another can facilitate operation of the securement device and/or can reduce separation of one or more of the adhesive dressings 331, 332 from the clamp 310 that might otherwise occur (e.g., in some embodiments where a single dressing is attached to both branches 311, 312 of the clamp 310). In some embodiments, no portion of either adhesive dressing 331, 332 overlaps the other adhesive dressing 331, 332 when the securement device 109 is transitioned to the closed orientation (see FIG. 14F). In other embodiments, at least a portion of one adhesive dressing 331, 332 may overlap at least a portion of the other adhesive dressing 331, 332 when the securement device 109 is in the closed orientation.

Figure 8:
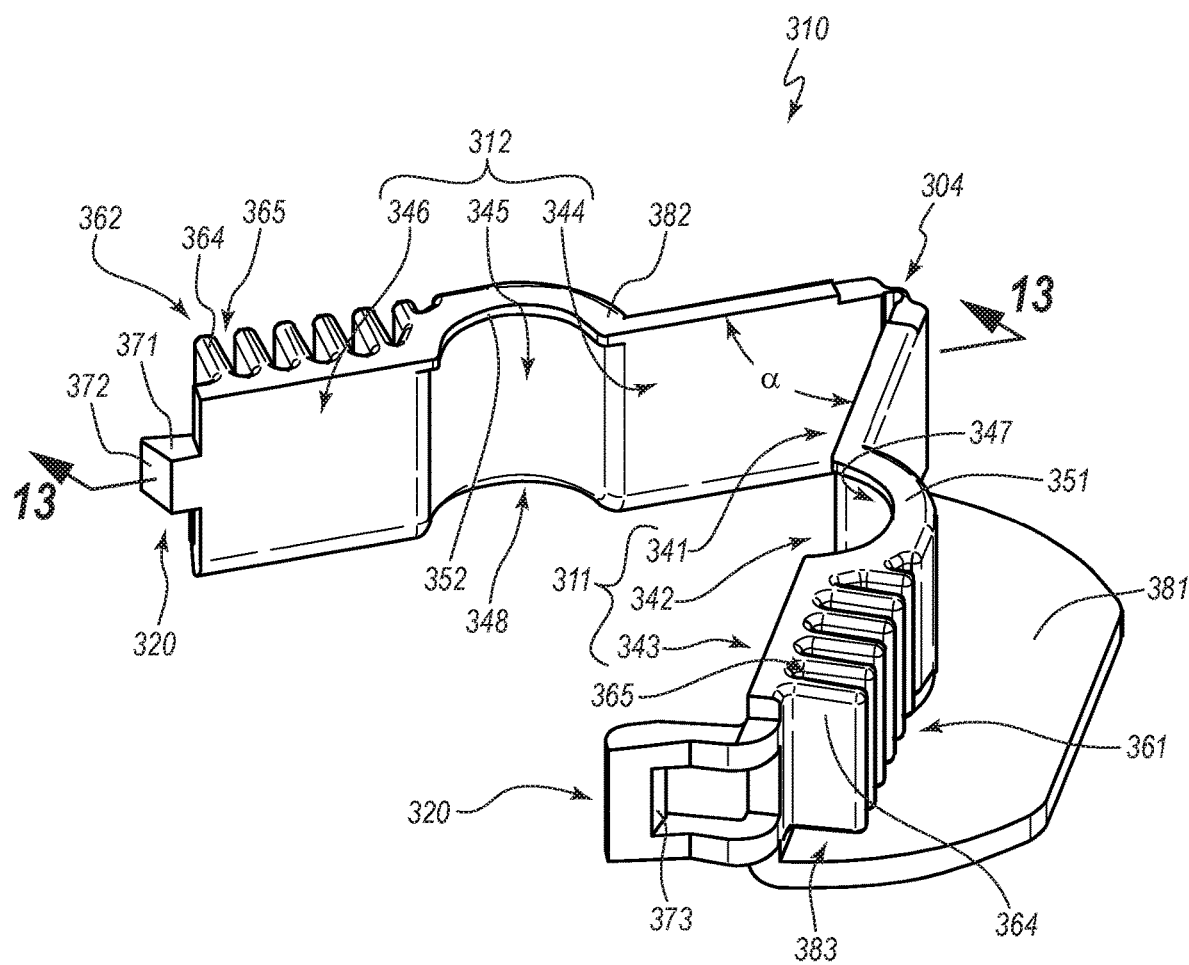
FIG. 8 is a perspective view of an embodiment of a clamp portion of the securement device of FIG. 7 that is depicted in the open orientation.

FIG. 8 is a perspective view of an embodiment of the clamp 310 in an open orientation, which can correspond to the open orientation of the securement device 109. In the illustrated embodiment, the first and second branches 311, 312 define an angle α relative to each other. In various embodiments, the angle α can be altered through a large range as the first and second branches 311, 312 rotate relative to each other about the hinge 304. For example, in various embodiments, the angle α can be within a range from about 0 to about 360, about 0 to about 270, about 0 to about 180, or about 0 to about 90 degrees.

Figure 9:
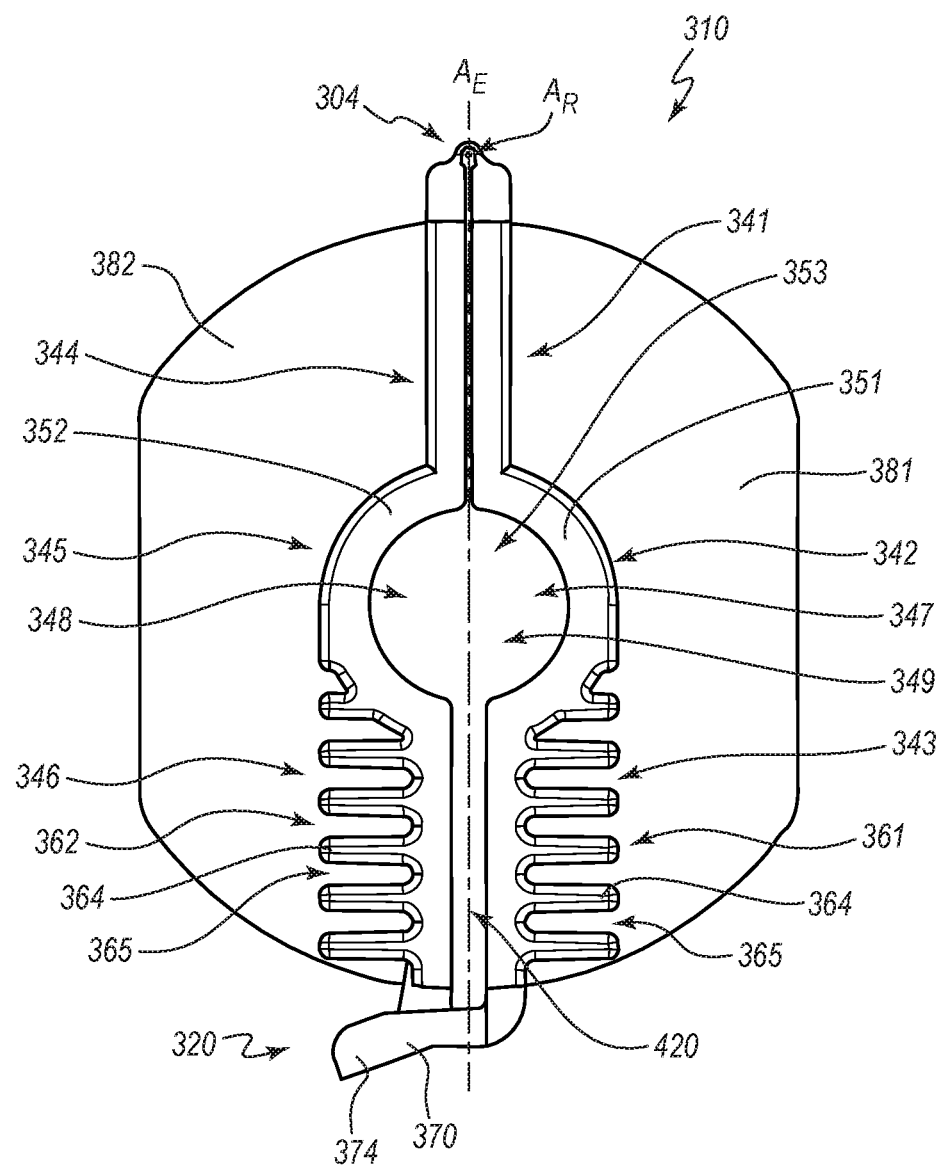
FIG. 9 is a top plan view of the clamp depicted in a closed orientation.

With reference to FIGS. 8 and 9, in some embodiments, transitioning the clamp 310 to the closed state (FIG. 9)

involves rotating the first and second branches 311, 312 into close proximity to each other such that the angle α is 0 degrees or about 0 degrees, or stated otherwise, such that inner arms 341, 344 of the first and second branches 311, 312, respectively, are parallel or substantially parallel to each other. In some embodiments, at least a portion of the inner arms 341, 344 can touch each other when the clamp 310 is in the closed orientation, whereas in other embodiments, the inner arms 341, 344 may remain fully spaced apart and not touch one another when the clamp 310 is in the closed orientation.

The first branch 311 can include the inner arm 341, a receptacle 342, and an outer arm 343. Similarly, the second branch 312 can include the inner arm 344, a receptacle 345, and an outer arm 346. The terms "inner" and "outer," as used in this context, refer to the arrangement depicted in FIG. 8. These terms can alternatively refer to proximity to the hinge 304 (with inner being closer to the hinge 304) or to proximity to an elongated central axis of the clamp 310 (e.g., the axis of elongation $A_E$ depicted in FIG. 9). Due to the angular arrangement of the first and second branches 311, 312 in FIG. 8, the inner arms 341, 344 are closer to the hinge 304, and as a result, are also closer to the elongated central axis of the clamp 310, as compared with the relative positions of the outer arms 343, 346. The terms are not intended to be restrictive. For example, other embodiments may not include a hinge 304, such that proximity to a hinge is rendered meaningless, and the "inner" and "outer" arms may at times be equidistant from the elongated central axis. For example, in some embodiment, the hinge 304 is replaced with any suitable locking mechanism (such as a duplicate of the lock 320), which may be fully releasable, and the first and second branches 311, 312 may be fully separable from each other.

In the illustrated embodiment, the inner arms 341, 344 are each attached at one end thereof to the hinge 304. Each of the inner arms 341, 344 extends away from the hinge 304 toward an opposite end thereof, which opposite end is attached to the receptacle 342 or the receptacle 345, respectively.

With reference to FIGS. 8 and 9, in the illustrated embodiment, the receptacles 342, 345 are curved regions that are outwardly or convexly bowed relative to an axis of elongation $A_E$ of the clamp 310, when the clamp 310 is in the closed orientation. Each receptacle 342, 345 defines a recess or cavity 347, 348, respectively, into which at least a portion of the needle hub 140 can be received. The cavities 347, 348 collectively define a cavity 349 (FIG. 9) of the clamp 310. Each receptacle 342, 345 can include an inner surface that contacts a portion of the needle hub 140 when the clamp 310 is in the closed orientation. In the illustrated embodiment, the inner surfaces are each substantially semi-cylindrical (see FIG. 8). Other suitable shapes and configurations are contemplated (e.g., polygonal prismatic, oval cylindrical).

With continued reference to FIGS. 8 and 9, the receptacles 342, 345 can include stops 351, 352, such as any suitable inward protrusions (e.g., barriers, ridges, lips, or shoulders), at upper ends of the cavities 347, 348. The illustrated stops 351, 352 are shoulders, and thus are also referred to as such. The shoulders 351, 352 can extend radially inward. In some embodiments, the shoulders 351, 352 can serve as a backup or redundant safety mechanism that can prevent inadvertent removal of the needle hub 140 from the cavity 349 when the clamp 310 is in the closed orientation. For example, the shoulders 351, 352 can extend inwardly 351 to define a restricted opening 353 at an upper end of the cavity 349. In the illustrated embodiment, the opening is substantially circular. A diameter of the opening 353 can be smaller than an outer diameter of any suitable region of the needle hub 140, such that the needle hub 140 may only be retracted proximally through the opening 353 up to the designated region when the clamp 310 is in the closed orientation. For example, in the illustrated embodiment, the opening 353 may define a slightly smaller diameter than the shoulder region 153 of the needle hub 140 (see FIGS. 4 and 5). The shoulders 351, 352 of the clamp 310 thus may prevent at least the shoulder region 153 of the needle hub 140, and the portion of the needle hub 140 that is distal thereto, from being inadvertently retracted through the opening 353 when the clamp 310 is in the closed orientation (e.g., when the clamp 310 is secured to the skin of a patient). Stated otherwise, the shoulders 351, 352 can delimit proximal movement of the needle hub 140 relative to the clamp 310.

With continued reference to FIGS. 8 and 9, each of the outer arms 343, 346 is attached at a first end thereof to one of the receptacles 342, 345, respectively. The outer arms 343, 346 extend away from the receptacles 342, 345 and, in the illustrated embodiment, are each attached at an opposite end thereof to a portion of the lock 320.

In various embodiments, one or more the outer arms 343, 346 can include a grip 361, 362 that can aid in transitioning the clamp 310 from the open orientation to the closed orientation. In the illustrated embodiment, the grips 361, 362 are also partially defined by the receptacles 342, 345. The grips 361, 362 can be configured for ready manipulation by a user, and may be the preferred site of the clamp 310 at which a user can apply pressure or inwardly directed forces to close the clamp 310.

In the illustrated embodiment, each grip 361 includes a plurality of laterally extending fins 364 that define spaces 365 therebetween. The fins 364 extend transversely away from the axis of elongation $A_E$. In the illustrated embodiment, the fins 364 terminate at a fixed distance from the axis of elongation $A_E$ such that the free tips of the fins 364 are substantially coplanar. In other embodiments, the fins 364 may extend to different distances from the axis of elongation $A_E$. The fin 364-and-space 365 arrangement can advantageously reduce the amount of material that might otherwise be used in forming gripping surfaces that are spaced from the axis of elongation $A_E$.

In some embodiments, the fin 364-and-space 365 arrangement preserves a flexibility of the arms 343, 346. For example, as can be seen in FIG. 9, a thickness of the arms 343, 346 at the base ends of the fins 364 is substantially the same as a thickness of the arms 341, 344. Stated otherwise, an effective beam width of the arms 343, 346 is substantially the same as an actual beam width of the arms 341, 344. The fin 364-and-space 365 arrangement thus can permit flexure of the arms 343, 346 in a manner similar to flexure of the arms 341, 344. In some embodiments, a flexibility (e.g., flexural strength) of the arms 343, 346 about an axis parallel to the axis of rotation $A_R$ (FIG. 9) of the clamp 310 may be substantially the same as the flexibility of the arms 341, 344. In other embodiments, the grips 361, 362 may instead be solid, thus increasing the thickness of the arms 343, 346 without adjusting a flexibility of the arms 343, 346. In certain of such embodiments, the arms 343, 346 may be significantly less flexible than the arms 341, 344.

Figure 10:
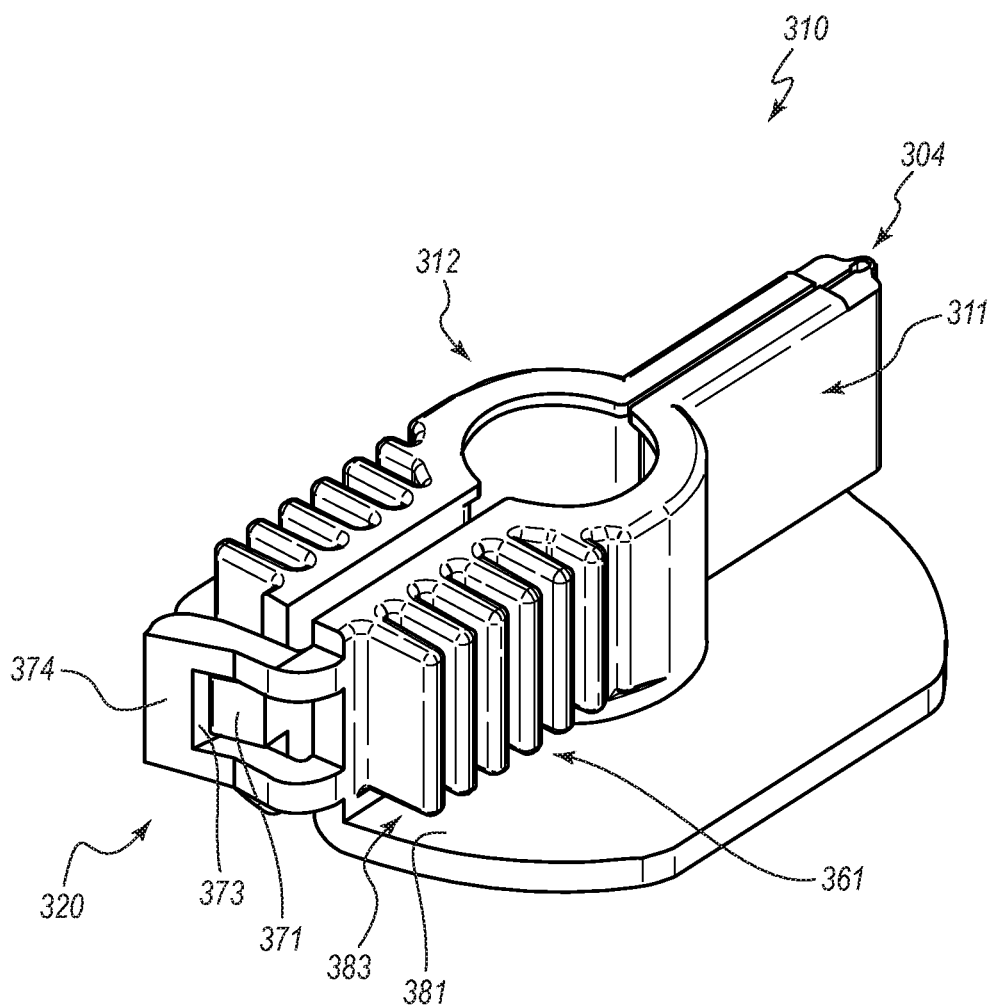
FIG. 10 is a perspective view of the clamp in the closed orientation.

With reference to FIGS. 8-10, in the illustrated embodiment, the lock 320 at the ends of the arms 343, 346 comprises a latching mechanism that includes a latching arm or latch 370 and a catch 371. The latch 370 can be configured to selectively attach to and detach from the catch 371. In the illustrated embodiment, the latch 370 is automatically secured to the catch 371 as the clamp 310 is transitioned from the open configuration to the closed configuration. In particular, the catch 371 includes an angled surface 372 that interacts with a leading edge of the latch 370 to deflect the latch 370 outwardly relative to the hinge 304, or downwardly in the orientation shown in FIG. 9, as the clamp 310 is closed. The latch 370 can be resiliently flexible, such that upon sufficient closure of the clamp 310, the latch 370 snaps inwardly, or upwardly in the orientation shown in FIG. 9, and a retaining surface 373 is held in place by the catch 371. When the lock 320 is in the configuration shown in FIG. 9, it may be referred to as being locked, engaged, or secured.

The illustrated lock 320 is selectively releasable. In particular, when the clamp 310 is in the closed orientation of FIGS. 9 and 10, the latch 370 can be deflected outward (downward in FIG. 9) to disengage the latch 370 from the catch 371, thereby permitting the first and second branches 311, 312 to be separated from each other. In particular, in the illustrated embodiment, the latch 370 includes an enlarged retainer portion 374 under which a practitioner may situate a portion of a finger or other instrument in order to pry or pull the latch 370 away from the catch 371 to undo the lock 320. This may be desirable in some embodiments, as it may be advantageous to remove the clamp 310 from the needle assembly 104 to thereafter permit direct removal of the needle assembly 104 from the patient. In other instances, the clamp 310 may remain engaged with the needle assembly 104 during removal of the needle assembly 104 from the patient. For example, with the clamp 310 engaged to the clamp 310, a practitioner may grip the clamp 310 and pull proximally, or away from the patient, to remove the needle assembly 104 from the patient.

Any suitable locking mechanism is contemplated for the lock 320, whether of a selectively releasable or permanent variety. For example, in some embodiments, the lock 320 is a one-way lock, rather than a selectively releasable lock, that permits the clamp 310 to transition from the open state to the closed or locked state, but prevents the clamp 310 from being transitioned from the locked state to the open state. For example, in some embodiments, the retainer portion 374 may be significantly smaller so as to prevent ready manipulation thereof, or may otherwise may be configured to prevent or inhibit unlocking of the lock 320. In certain of such embodiments, the clamp 310 and the needle assembly 104 can be removed simultaneously from a patient, such as by grasping and pulling on the clamp 310.

With reference to FIGS. 8-11, the clamp 310 can define one or more platforms or lateral protrusions 381, 382 that extend transversely from the first and second branches 311, 312, respectively. For example, in the illustrated embodiment, the lateral protrusions 381, 382 extend outwardly from a base end of the first and second branches 311, 312, respectively. As further discussed below, the dressings 331, 332 can be secured to the lateral protrusions 381, 382.

Figure 11:
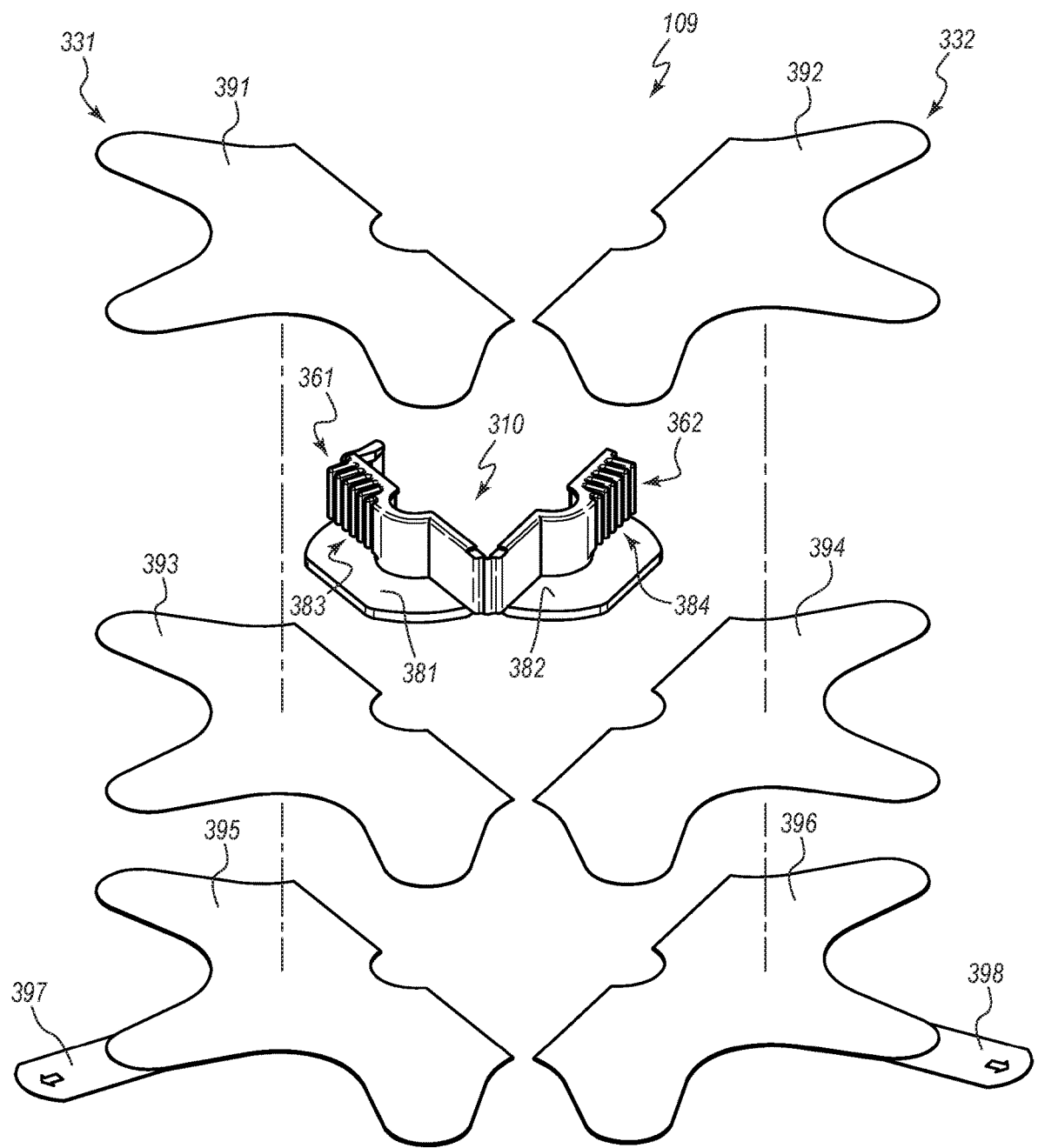
FIG. 11 is an exploded perspective view of the securement device of FIG. 7 depicted in the open orientation.

As shown in FIGS. 8, 9, and 11, in the illustrated embodiment, the clamp 310 can define a gap 383 between the grip 361 and the lateral protrusion 381. As shown in FIG. 11, the clamp 310 similarly can define a gap 384 between the grip 362 and the lateral protrusion 382. In some embodiments, the gaps 383, 384 render the outer arms 343, 346 of the first and second branches more flexible than they would otherwise be if the lower end of the grips 361, 362 were attached to (e.g., integral with) the lateral protrusions 381, 382. Stated otherwise, the gaps 383, 384 may increase the flexibility of or a degree of freedom of movement of the outer arms 343, 346, which may facilitate a closure event. In other or further instances, the gaps 383, 384 may be beneficial for increasing a contact area over which the dressings 331, 332 are secured to the lateral protrusions 381, 382.

With continued reference to FIG. 11, the dressings 331, 332 can each include a plurality of components. In the illustrated embodiment, the dressing 331 includes an upper layer 391, a lower layer 393, and a liner 395 that are secured together in any suitable fashion, such as via one or more adhesives. Similarly, the dressing 332 includes an upper layer 392, a lower layer 394, and a liner 396 that are secured together in any suitable fashion. In some embodiments, the various layers 391, 392, 393, 394 are formed as flexible films. Each of the liners 395, 396 can be formed as a folded sheet, with a fold thereof positioned at an interior side of the sheet. Each liner 395, 396 can include a pull tab 397, 398, which can be attached to a lower section of the folded sheet.

In the illustrated embodiment, each upper layer 391, 392 has an adhesive coating on an underside thereof and each lower layer 393, 394 has an adhesive coating on each of an upper side and lower side thereof. The upper layers 391, 392 and the lower layers 393, 394 can be affixed to each other with the lateral protrusions 381, 382 of the clamp 310 sandwiched therebetween. Portions of the upper layers 391, 392 can be inserted into the gaps 383, 384 prior to being adhered to the lateral protrusions 381, 382. The upper sections of the liners 395, 396 can be releasably adhered to the adhesive coatings of the lower layers 393, 394, with the lower sections of the liners 395, 396 being unsecured thereto. Accordingly, the liners 395, 396 can be removed from the lower layers 393, 394 by pulling outwardly on the pull tabs, which causes the liners 395, 396 to peel away from the lower layers 393, 394. The peeling begins at the inner edges of the liners 395, 396, at the position the liners 395, 396 are folded, and then moves outwardly.

In the illustrated embodiment, each of the dressings 331, 332 includes a plurality of projections, such that when the dressings 331, 332 are approximated to each other (see FIG. 14F), they substantially form a star shape. In the illustrated embodiment, each dressing 331, 332 includes three arms or prongs, thus defining a six-armed star shape when the securement device 109 is in the closed orientation. In some instances, a multi-armed dressing arrangement can advantageously permit the dressings to adapt or conform to the contours of a patient, such as to the skin of a shoulder or leg. Other suitable shapes for the dressings 331, 332 are contemplated.

Figure 12:
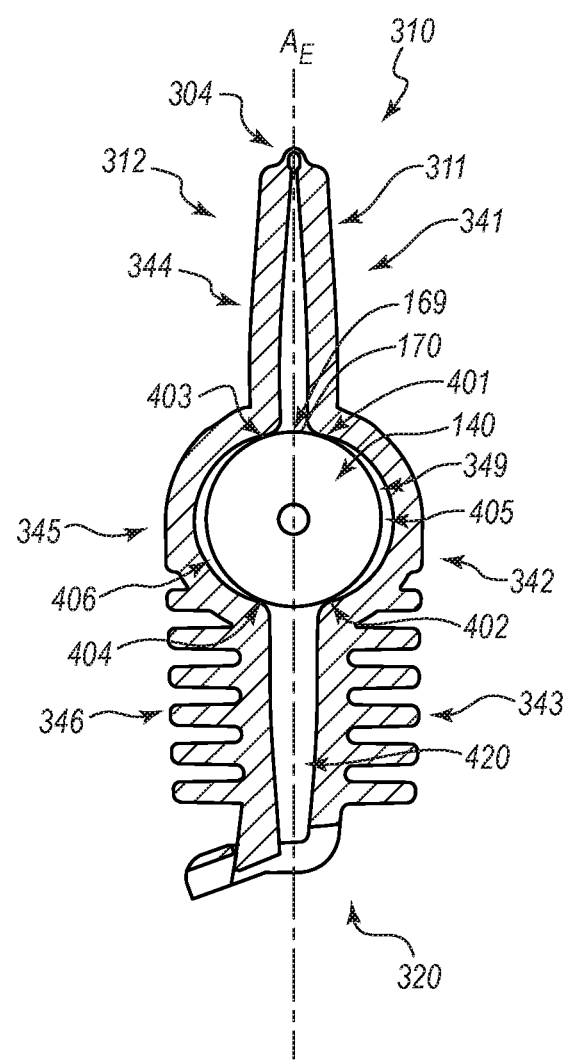
FIG. 12 is a cross-sectional view of an embodiment of the clamp being bowed after the clamp has been closed about an embodiment of a cannula hub.

FIG. 12 is a cross-sectional view of the clamp 310 in the locked orientation about the needle hub 140. When the clamp 310 is secured to the needle hub 140, at least a portion of one or both of the first and second branches 311, 312 can be bent. For example, at least a portion of one or both of the first and second branches 311, 312 can be formed of a flexible or resiliently flexible material (e.g., any suitable plastic, such as, for example, polypropylene) that can deform as the clamp 310 is transitioned from the open orientation to the closed orientation due to interaction or interference between portions of the first and second branches 311, 312 and the needle hub 140. Stated otherwise, in various embodiments, at least a portion of the first and/or the second branch 311, 312 transitions from a relaxed state to a deformed state, deflected state, or flexed state as the clamp 310 is closed about the needle hub 140. In certain embodiments that are resiliently flexible, these portions of the first and/or the second branches 311, 312 can automatically transition from the deformed state, deflected state, or flexed state back to the relaxed state as the clamp is opened and no longer interacts with the needle hub 140.

In the illustrated embodiment, when the clamp 310 is transitioned to the closed orientation, each of the inner arms 341, 344 and the outer arms 343, 346 of the first and second branches 311, 312 is deformed, deflected, or flexed. In particular, as can be seen in FIG. 8, when the clamp 310 is in the open orientation, each of the inner arms 341, 344 and the outer arms 343, 346 includes an inner surface that is substantially flat or planar, or stated otherwise, is substantially noncurved. Moreover, substantially an entirety of the inner arms 341, 344 is linear or noncurved when the clamp 310 is in the open orientation, and in further embodiments, maintains the same shape when the clamp 310 is closed without the needle hub 140 being positioned therein, as shown in FIG. 9. In such instances, substantially an entirety of an inwardly facing surface of the inner arms 341, 344 can be flat or planar and can be parallel to or collinear with the axis of elongation $A_E$. Similarly, an inner portion of each outer arm 343, 346—in particular, the portion of the outer arm 343, 346 from which the grip 361, 362 extends—is likewise substantially linear or substantially noncurved when the clamp 310 is in the open orientation, or is in the closed orientation without the needle hub 140 being positioned therein as shown in FIG. 9.

Once the clamp 310 has been transitioned to the closed orientation about the needle hub 140, the portions of the inner arms 341, 344 and the outer arms 343, 346 that were substantially linear are instead curved (see FIG. 12). In the illustrated embodiment, the substantially linear condition corresponds with a low-energy state or relaxed state, whereas the curved state corresponds with a high-energy state, tensioned state, or flexed state. The curvature of the inner surfaces of the arms 341, 343, 344, 346, as depicted in FIG. 12, may be exaggerated relative to an amount of curvature actually present in some embodiments.

Although all four arms 341, 343, 344, 346 are configured to deform in the illustrated embodiment, only one, two, or three of the arms 341, 343, 344, 346 may deform in other embodiments. For example, in some embodiments, one of the branches 311, 312 may be formed of a substantially inflexible material and/or may have a configuration that is less prone to deformation, while the other of the branches 311, 312 may be flexible and/or significantly more prone to deformation. Accordingly, one set of arms 341, 343 or 344, 346 may be configured to bend, whereas the other set of arms 341, 343 or 344, 346 may be configured to remain unbent when the clamp 310 is closed about the needle hub 140. In still other embodiments, only one of the arms 341, 343, 344, 346, or a portion thereof, may be configured to bend or otherwise flex when the clamp 310 is closed about the needle hub 140.

In other or further embodiments, one or more of the receptacles 342, 345 may deform or flex as the clamp 310 is transitioned to the closed orientation to engage the needle hub 140. For example, in the illustrated embodiment, as the curved receptacles 342, 345 are pressed against the needle hub 140, four contact regions 401, 402, 403, 404 defined by the receptacles 342, 345 contact the needle hub 140. More particularly, the contact regions 401, 402, 403, 404 contact the coupling region 169 of the needle hub 140, or even more particularly, contact the maximum transverse perimeter 170 of the needle hub 140. In the illustrated embodiment, the maximum transverse perimeter 170 is substantially circular, and defines a diameter that is slightly larger than a diameter of the cavity 349 (which is defined by the interior surfaces of the receptacles 342, 345). Stated otherwise, a radius of curvature of the maximum transverse perimeter 170 can exceed a radius of curvature of the interior surfaces of the receptacles 342, 345. This can yield gaps 405, 406 between the receptacles 342, 345 and the needle hub 140. The gaps 405, 406 depicted in FIG. 12 may be exaggerated relative to an actual size thereof, for some embodiments. In some embodiments, the contact regions 401, 402 of the first branch 311 may spread slightly apart from one another, and the contact regions 403, 404 of the second branch 312 may spread slightly apart from one another, as the clamp 310 is closed around the needle hub 140. The receptacles 342, 345 thus may be resiliently deformed or flexed in a manner that tends to urge each contact region 401, 402, 403, 404 toward an interior of the needle hub 140. For example, the contact regions 401, 403 may be biased in a substantially downward direction while the contact regions 402, 404 may be biased in a substantially upward direction, in the orientation depicted in FIG. 12. The resilient deformation of the receptacles 342, 345 thus may yield gripping forces on the needle hub 140.

In other embodiments, a radius of curvature of the needle hub 140 is the same as or less than a radius of curvature of one or more of the receptacles 342, 345. For example, in some embodiments, the receptacles 342, 345 may be substantially complementary to the maximum transverse perimeter 170 or may be larger than the maximum transverse perimeter 170, which may eliminate or bifurcate each of the gaps 405, 406. In still other embodiments, the receptacles 342, 345 may define any other suitable shape or configuration and may contact or otherwise interact with any suitable portion of the needle hub 140 in any suitable manner.

In some embodiments, only the receptacles 342, 345 resiliently deform, whereas the arms 341, 343, 344, 346 do not deform, as the clamp 310 is transitioned to the closed state about the needle hub 140. In other embodiments, one or more of the receptacles 342, 345 resiliently deform and one or more of the arms 341, 343, 344, 346 resiliently deform as the clamp 310 is transitioned to the closed state. In still other embodiments, neither of the receptacles 342, 345 resiliently deform as the clamp 310 is transitioned to the closed state.

In various embodiments, the contact regions 401, 402, 403, 404 may extend over a larger portion of the maximum transverse perimeter 170 of the needle hub 140 than is shown in FIG. 12. For example, in various embodiments, the contact regions 401, 402, 403, 404 may collectively contact or cover no less than about 20, 25, 30, 40, 50, 60, 75, or 90 percent of the maximum transverse perimeter 170.

In some embodiments, most, substantially all, or all of the gripping force applied by the contact regions 401, 402, 403, 404 is due to bias provided by the flexed arms 341, 343, 344, 346. Stated otherwise, in some embodiments, relatively little or no gripping force provided by the clamp 310 is generated by deformation of one or more of the receptacles 342, 345, and most or all of the gripping force provided by the clamp 310 is generated by flexion of one or more of the arms 341, 343, 344, 346. As previously discussed, one or more of the arms 341, 343, 344, 346 can be resiliently deformed as the clamp 310 is attached to the needle hub 140. In the illustrated embodiment, each arm 341, 343, 344, 346 assumes the bowed configurations schematically depicted in FIG. 12. The arms 341, 343, 344, 346 thus may be resiliently deformed or flexed in a manner that tends to urge each contact region 401, 402, 403, 404 toward an interior of the needle hub 140. For example, the contact regions 401, 403 may be biased substantially toward each other, or in substantially leftward and rightward directions in the orientation of FIG. 12, via the arms 341, 344, respectively. Similarly, the contact regions 402, 404 may be biased substantially toward each other, or in substantially leftward and rightward directions in the orientation of FIG. 12, via the arms 341, 344, respectively. More generally, the flexed arms 341, 343 can bias the receptacle 342 inwardly, or toward the needle hub 140, and the flexed arms 344, 346 can bias the receptacle 345 inwardly, or toward the needle hub 140. The bias thus provided may be continuous while the clamp 310 remains in the closed or locked state. The resilient deformation of the receptacles arms 341, 343, 344, 346 thus may yield gripping or clamping forces on the needle hub 140.

The clamp 310 thus can grip the needle hub 140 to maintain the needle hub 140 in a fixed relationship relative to the clamp 310 when the clamp is in the closed orientation. Accordingly, when the dressings 331, 332 are affixed to a patient at an attachment site, the securement device 109 is able to secure the needle assembly 105 in fixed relationship relative to the attachment site.

With continued reference to FIG. 12, in the illustrated embodiment, the lock 320 and the hinge 304 are positioned at opposite ends of the clamp 310. Stated otherwise, the lock 320 is angularly spaced from the hinge 304 by 180 degrees. Stated in yet another manner, the lock 320 and the hinge 304 are substantially collinear and/or are aligned with the axis of elongation $A_E$ of the clamp 310. When the needle hub 140 is positioned within the cavity 349 and the clamp 310 is in the locked or closed orientation, the needle hub 140 is positioned between the lock 320 and the hinge 304.

In the illustrated embodiment, each elongated arm 341, 344 can advantageously provide a significant moment arm between the hinge 304 and the receptacles 342, 345, respectively; and more particularly, between the hinge 304 and the contact regions 401, 403. Similarly, each elongated arm 343, 346 can provide advantageously provide a significant moment arm between the receptacles 342, 345, respectively, and the lock 320; and more particularly, between each contact region 402, 404 and the lock 320. During closure of the clamp 310, the hinge 304 is a pivot about which the arms 341, 344 rotate, the contact regions 401, 403 are pivots about which the receptacles 342, 345 rotate, and the contact regions 402, 404 are pivots about which the arms 343, 346 rotate. Continued application of inwardly directed forces at the non-hinged ends of the first and second branches 311, 312 thus can deform or flex at least the arms 341, 343, 344, 346 to the illustrated bowed configuration. Securing these non-hinged ends via the lock 320 can maintain the first and second branches 311, 312 in the flexed state, which can provide a continuous inward bias that grips the needle hub 140. Stated otherwise, the clamp 310 may be secured to the needle hub 140 via purely frictional gripping. Stated in yet another way, the clamp 310 entraps the needle hub 140 with beam stresses that arise in the first and second branches 311, 312.

The clamp 310 may be sufficiently compliant to define an elongated, generally oval shape, such as depicted in FIG. 12, when in the closed state about the needle hub 140. In some embodiments, positioning the grips 361, 362 (see FIG. 9) at ends of the elongated first and second branches 311, 312 that is opposite the hinge 304 advantageously provides long moment arms that facilitate closure of the clamp 310.

In view of the foregoing, in various embodiments, the legs 341, 343, 344, 346 and/or an elongated configuration of the first and second branches 311, 312 can facilitate closure of the clamp 310 and/or and can yield stress forces that permit a versatile or accommodating friction-based connection to the needle hub 140 (as discussed further below with respect to FIG. 13). In various embodiments, the inner legs 341, 344 differ in length from the outer legs 343, 346 by no more than a factor of about 0.5, 0.75, 1.0, 1.25, 1.5, or 2.0. In some embodiments, one or more of the inner legs 341, 344 defines a length that is no less than about 0.1, 0.2, 0.3, 0.4, 0.5, or 0.6 times an overall length of the clamp 310, when the clamp 310 is in an empty, closed orientation such as depicted in FIG. 9. In some embodiments, one or more of the outer legs 343, 346 defines a length that is no less than about 0.1, 0.2, 0.3, 0.4, 0.5, or 0.6 times an overall length of the clamp 310, when the clamp 310 is in the empty, closed orientation. In various embodiments, one or more of the inner legs 341, 344 defines a length that is no less than about 0.25, 0.5, 0.75, 1, 1.25, 1.5, 1.75, or 2.0 times a length of a diameter D of the cavity 349 defined by the receptacles 342, 345 (see FIG. 13). In various embodiments, one or more of the outer legs 343, 346 defines a length that is no less than about 0.25, 0.5, 0.75, 1, 1.25, 1.5, 1.75, or 2.0 times a length of a diameter D of the cavity 349 defined by the receptacles 342, 345 (see FIG. 13).

In some embodiments, the clamp 310 may be devoid of dedicated or curved receptacles, such as the receptacles 342, 345. For example, the clamp 310 may include first and second branches that do not, when in a natural or relaxed state, define recessed regions into which portions of the hub 140 can be received. Rather, portions of the first and second branches may conform to a portion of the external surface of the needle hub 140 as the first and second branches are closed about the needle hub 140. For example, in some embodiments, the first and second branches 311, 312 may be substantially linear elements with flat internal surfaces, and contact regions of the first and second branches 311, 312 may curve to match at least a portion of an outer contour of the needle hub 140 as the clamp 310 is closed. These curved contact regions may be biased toward the needle hub 140 by stress forces that arise in the first and second branches 311, 312 during such closure, as previously described.

With reference to FIGS. 9 and 12, in the illustrated embodiment, the inner faces of the arms 343, 346 define a gap 420 that can facilitate closure of the clamp 310 and securement of the lock 320. As shown in FIGS. 8 and 9, in the absence of the needle hub 140, the inner faces of the arms 343, 346 can be substantially planar, such that when the clamp 310 is closed, the planar faces are substantially parallel to each other. However, as shown in FIG. 12, when the clamp 310 is closed around the needle hub 140, these planar faces are bowed, such that the locking ends of the arms 343, 346 are closer together than are the ends that are adjacent to the needle hub 140. The gap 420 can permit the locking ends of the arms 343 to be brought into contact with each other during a closure event, which can facilitate closure and locking of the clamp 310. For example, in certain embodiments where the locking mechanism comprises the latch 370 and the catch 371 (see FIG. 8), the extra space afforded by the gap 420 can provide sufficient clearance to ensure that the latch 370 snaps back into a non-deflected state after having passed over the catch 371.

Figure 13:
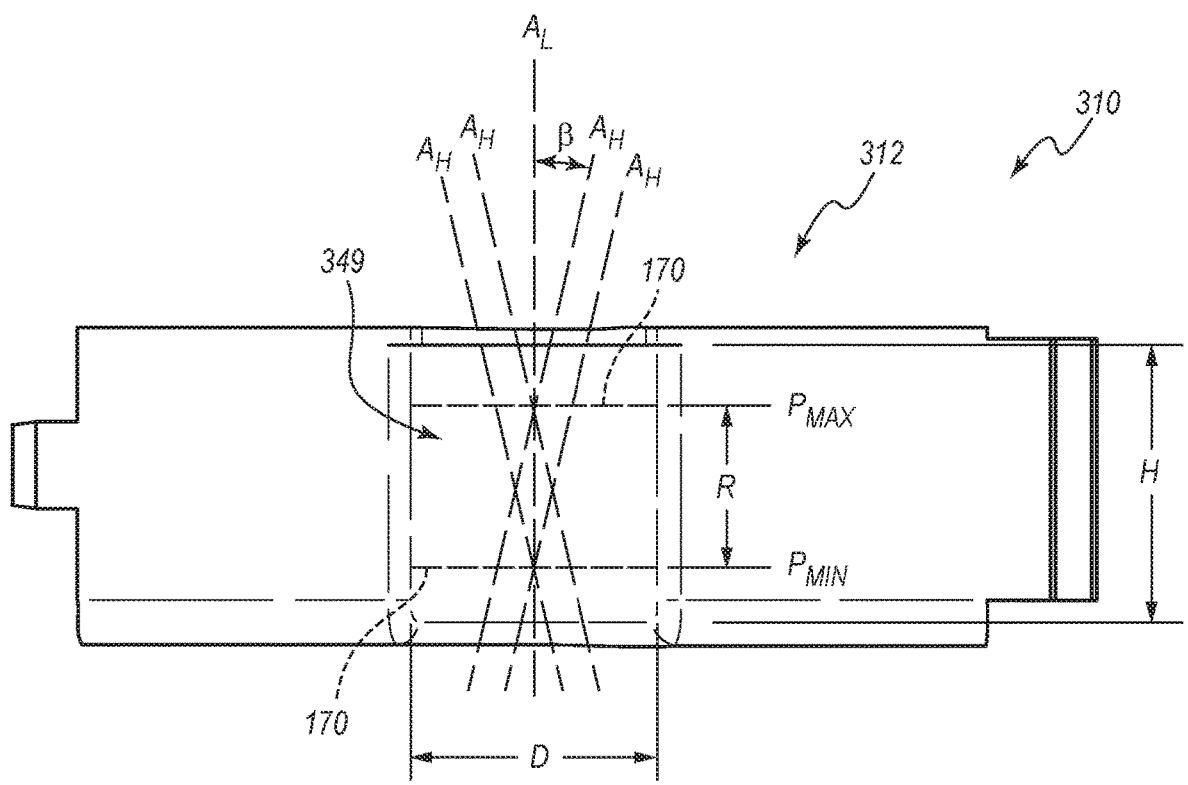
FIG. 13 is a cross-sectional view of the clamp taken along the view line 13-13 in FIG. 8, which effectively shows an interior of a branch of the clamp in elevation.

With reference to FIG. 13, the clamp 310 can couple with the needle hub 140 in any of a variety of different relative orientations. In particular, frictional or gripping interaction between the clamp 310 and the needle hub 140, as previously described, can permit the needle hub 140 to be positioned at a variety of different heights and/or at a variety of different angles relative to an insertion site in the skin of a patient.

The cavity 349 defined by the clamp 310 can have a height H and can define a central longitudinal axis $A_L$. In the illustrated embodiment, a bottom surface of the clamp 310 is substantially flat and extends along a plane that is substantially orthogonal to the longitudinal axis $A_L$. Accordingly, if the bottom surface of the clamp 310 rests flatly, or in good contact, with a substantially flat skin surface, the longitudinal axis $A_L$ will be substantially aligned with a surface normal of the skin surface. The clamp 310 can be securely coupled with the needle hub 140 within a range of heights relative to the skin surface and/or a variety of angles relative to the longitudinal axis $A_L$.

The full range of suitable heights relative to the skin surface is depicted by the span R in FIG. 13. In various embodiments, the span R is no less than about 0.1 inches, 0.25 inches, 0.5 inches, 0.75 inches, or 1 inch. In other or further embodiments, the span R is no less than about 25, 50, 75, or 90 percent of a total height H of the chamber 349.

The full range of suitable angles relative to the longitudinal axis $A_L$ is depicted by the span β in FIG. 13. in various embodiments, the span β is no less than about 15, 30, 45, or 60 degrees.

With continued reference to FIG. 13, as previously discussed, in some embodiments a diameter D of the cavity 329 is slightly smaller than a diameter of the maximum lateral perimeter 170 of the needle hub 140. In various embodiments, the diameter D may be no greater than 80, 85, 90, or 95 percent of the diameter of the maximum lateral perimeter 170.

In some embodiments, the clamp 310 may be simple and/or inexpensive to manufacture. For example, in some embodiments, the clamp 310 is formed a single unitary piece of material, which may be injection molded. Any of a variety of materials are contemplated, including a variety of plastics (e.g., polypropylene). In some embodiments, the hinge 304 is a living hinge.

FIGS. 14A-14G depict various stages of an illustrative method of using the intraosseous access system 100 of FIG. 1. The illustrative method is depicted in sequential order in FIGS. 14A-14G. Other methods may proceed in a different sequence with respect to some of the depicted stages. Moreover, one or more of the depicted stages may be omitted and/or one or more additional stages not depicted may be included in other or further methods.

FIG. 14A depicts the access assembly 106 in an assembled state. In some instances, the access system 106 is assembled by a practitioner or user in a stage that precedes that depicted in FIG. 14A. In other instances, the access assembly 106 may be preassembled. In the assembled state, the obturator assembly 102 is coupled to the needle assembly 104.

As previously discussed, in the illustrated embodiment, the keyed coupling interfaces 137, 150 of the coupling hub 110 and the needle hub 140, respectively, can cooperate to ensure that a predetermined relationship between the obturator 103 and the needle 105 is achieved. Stated otherwise, the keyed coupling interfaces 137, 150 can ensure that the obturator 103 defines a fixed angular orientation relative to the needle 105. The coupling interfaces 137, 150 may likewise maintain the fixed angular orientation during rotation of the access assembly 106 during an insertion event, e.g., during rotation of the access assembly 106 via a driver (e.g., a drill).

With continued reference to FIG. 14A, during assembly of the access assembly 106, the arms or projections 132 can be advanced over the skirt 168 of the needle hub 140. The snap interface or inward protrusions 134 of the projections 132 can grip an underside of the skirt 168 to maintain the coupling hub 110 and the needle hub 140 in a coupled state. In the illustrated embodiment, the skirt 168 is shaped substantially as an outward protrusion, and the inner surface of the arm 132 substantially defines a recess into which the protrusion is received. In other embodiments, the protrusion/recess interface may be reversed. For example, the arm 132 may define a protrusion is received into a recess defined by the skirt 168 to couple the obturator hub 110 with the needle hub 140.

The projection 132 and the hub 168 may collectively be referred to as a releasable engagement mechanism 262. The releasable engagement mechanism 262 may be configured to keep the obturator hub 110 and the needle hub 140 coupled together during general manipulation of the access assembly 106, such as during removal from packaging and/or coupling thereof with a drill or other driver. The releasable engagement mechanism 262 may, however, provide a relatively weak coupling that is capable of being released upon application of sufficient removal force to the coupling hub 110 in a proximal direction, relative to the needle hub 140. For example, the releasable engagement mechanism 262 may provide a coupling force that tends to keep the coupling hub 110 engaged with the needle hub 140. When a proximally directed force exceeds the coupling force of the releasable engagement mechanism 262, the releasable engagement mechanism 262 can disengage and permit the coupling hub 110 to be withdrawn from the needle hub 140. In various embodiments, the coupling force (i.e., the force that counteracts a proximally directed force on the coupling hub 110) can be no greater than about 0.25, 0.5, 0.75, 1.0, 1.5, or 2.0 pounds.

In certain embodiments, the releasable engagement mechanism 262 provides a coupling force that is significantly lower than an embedding force between the needle 105 and a bone within which the needle 105 is inserted. Stated otherwise, the releasable engagement mechanism can be configured to permit the coupling hub 110 to be decoupled from the cannula hub 140, after the cannula hub 140 has been introduced into the bone, by imparting a proximally directed force on the coupling hub 110 that is smaller in magnitude than a force imparted on the cannula 204 by the bone that maintains the cannula 204 positioned in the bone.

Accordingly, in some embodiments, after introducing the access assembly 106 into the bone, a user may simply pull back, or proximally, on the obturator hub 110 with any amount of force that exceeds the coupling force of the releasable engagement mechanism 262, and the obturator hub 110 will automatically disengage from the needle hub 140. Further, the obturator hub 110 can be withdrawn from the needle hub 140 and the patient, and the needle hub 140 can remain in the bone. In some instances, the user can remove the hub 110 from the needle hub 140 using a single hand after the access assembly 106 has been introduced into the bone. Other suitable arrangements of the releasable engagement mechanism 262 are contemplated.

With continued reference to FIG. 14A, when the access assembly 106 is in the assembled state, the shield 167 can be coupled with each of the obturator 103 and the needle hub 140 in an unlocked state. In particular, a proximal end of the obturator 103 can define a larger diameter than does a recess 415. This larger diameter region of the obturator 103 can maintain the shield 167 in the unlocked state to permit the obturator 103 to translate relative to the shield 167 in a proximal direction when the user desires to remove the obturator hub 110 from the needle hub 140.

When the shield 167 is in the unlocked state, the arms are deflected outwardly, which can seat or otherwise position outward protrusions 421, 422 on resilient arms of the shield 167 within the groove 166 of the needle hub 140. The outward protrusions 421, 422 thus can cooperate with the groove 166 to maintain the shield 167 in a fixed longitudinal position relative to the needle hub 140 during the initial stages of withdrawal of the obturator 103 through the shield 167. In other embodiments, the groove 166 and the outward protrusions 421, 422 can be reversed.

In some embodiments, the needle hub 140 may define a low radial profile, which can be advantageous. For example, the maximum transverse perimeter 170 can be positioned internally relative to the obturator hub 110. Moreover, this same portion of the needle hub 140 is connected to the securement device 109 at later stages of the method, as discussed further below. Thus, the needle hub 140 can define a low profile that is less cumbersome for a patient and less susceptible to inadvertent contact that could disrupt the needle 105 after it has been inserted into the patient. The connection region 169 of the needle hub 140, which can define the maximum transverse perimeter 170 of the needle hub 140, thus may individually or sequentially connect with the obturator hub 110 during an early stage of the method, and individually or sequentially connect with the securement device 109 at a later stage of the method. In the illustrated embodiment, no portion of the needle hub 140 extends laterally outward beyond the maximum transverse perimeter 170. Stated otherwise, as viewed along a system rotational axis $A_{ROT}$, no portion of the needle hub 140 extends away from the rotational axis $A_{ROT}$ by a greater distance than does the maximum transverse perimeter 170 of the needle hub 140.

FIG. 14B is a cross-sectional view of the access assembly 106 after it has been used to provide access to an interior of a bone B of a patient P. For example, prior to the depicted stage, the access assembly 106 can be coupled with any suitable driver, and the user can then actuate the driver and press down to drill the needle 105 and the obturator 103 into the bone B. The driver can then be removed from the access assembly 106, leaving the access assembly 106 in place, as shown.

Figure 14C:
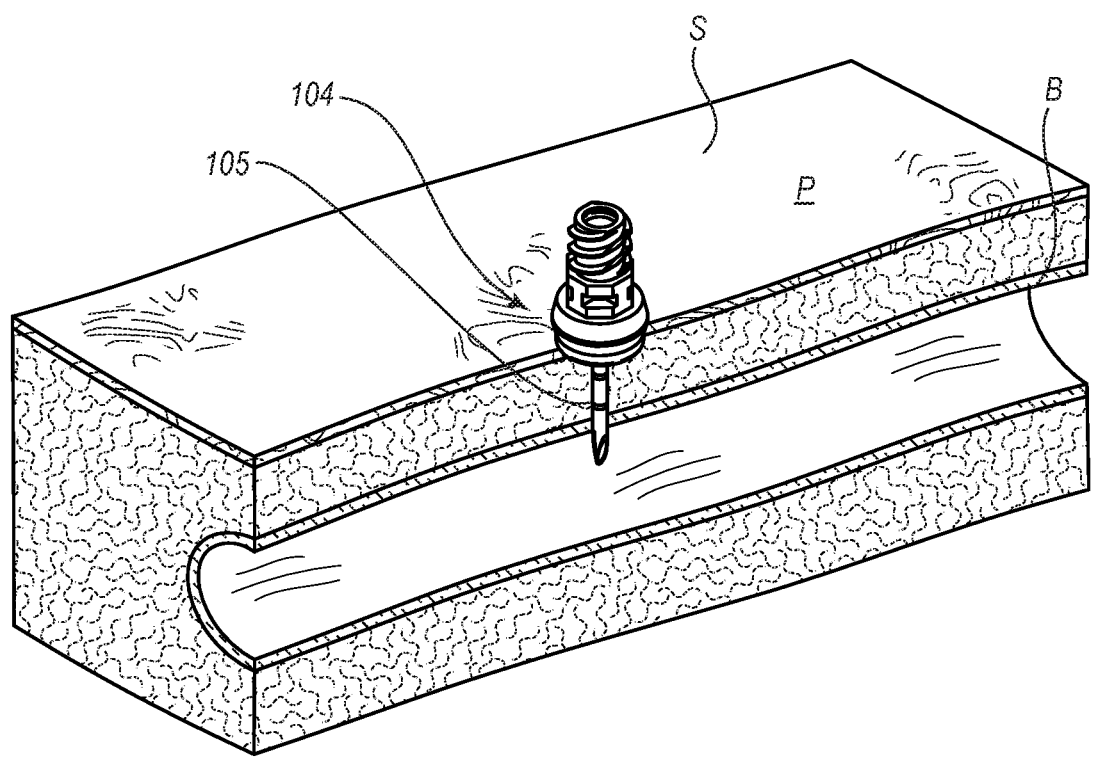
FIG. 14C is a perspective view of a later stage of the illustrative method in which the obturator assembly has been removed from the cannula assembly while the cannula assembly has been left in place in the bone of the patient.

FIG. 14C illustrates a stage after the obturator assembly 102 has been removed from the needle assembly 104, leaving the needle assembly 104 in place with the needle 105 remaining in the bone B of the patient P. In the illustrated embodiment, the obturator assembly 102 can be removed by pulling it in a proximal direction. In some embodiments removal of the obturator assembly 102 causes the shield 167 to slide distally along the obturator 103 and clamp onto a distal end of the obturator 103 (e.g., spring-loaded arms snap into the recess 415, as shown in FIG. 14A) to prevent inadvertent contact with the obturator tip.

Figure 14D:
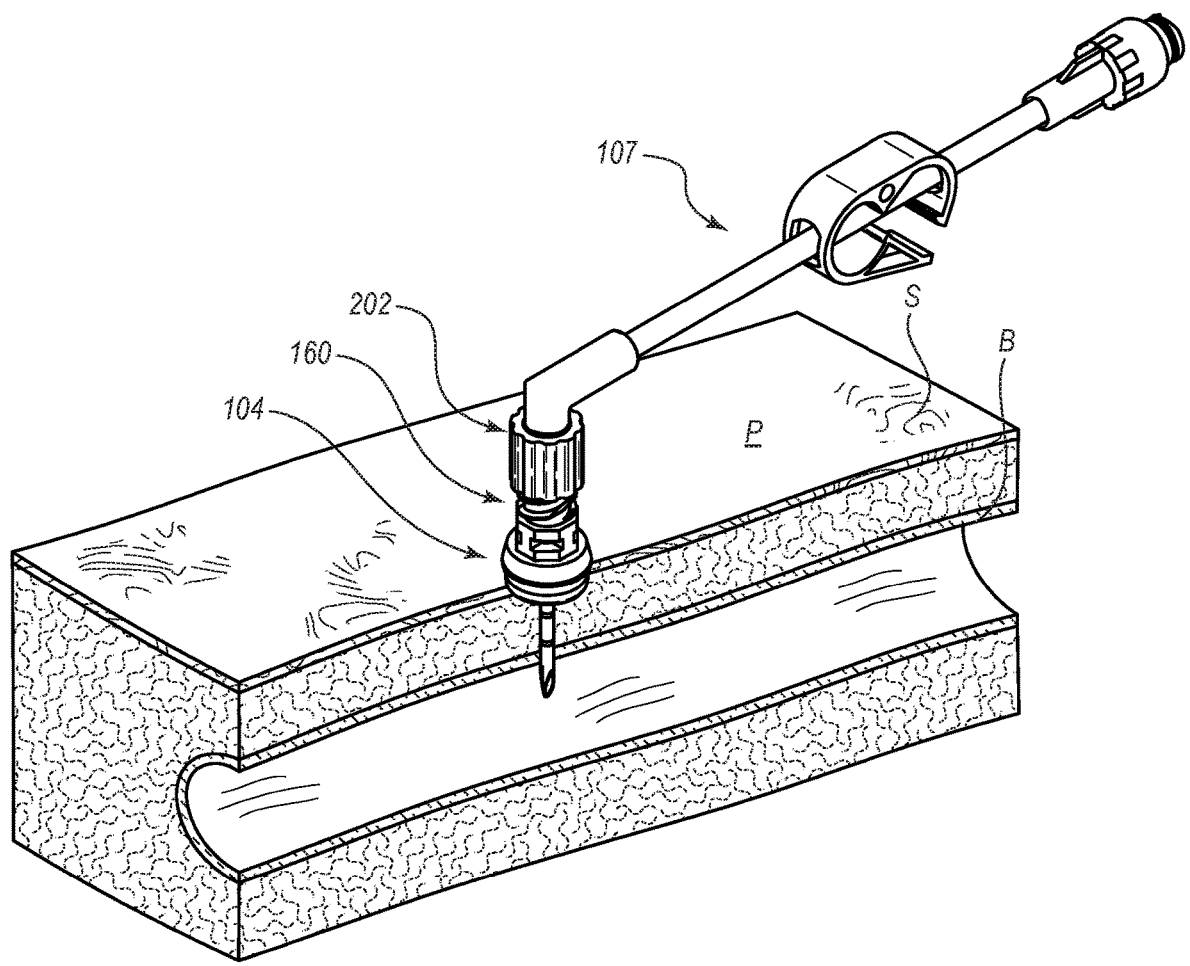
FIG. 14D is a perspective view of a later stage of the illustrative method in which the extension assembly is coupled to the cannula assembly.

FIG. 14D is a perspective view of a later stage of the illustrative method in which the extension assembly 107 is coupled to the needle assembly 104. In particular, the connector 202 of the extension assembly 107 is coupled to the connector 160 of the needle assembly 104. In some instances, it may be desirable to connect the extension assembly 107 to the needle assembly 104 quickly after the needle assembly 104 has been inserted into the bone B. Doing so may, for example, permit rapid delivery of critical drugs and/or other fluids to the patient P in emergency situations. Accordingly, in some instances, it can be desirable to achieve fluid communication with an interior of the bone B, such as via the extension assembly 107, prior to coupling the securement device 109 to the needle hub 140.

Figure 14E:
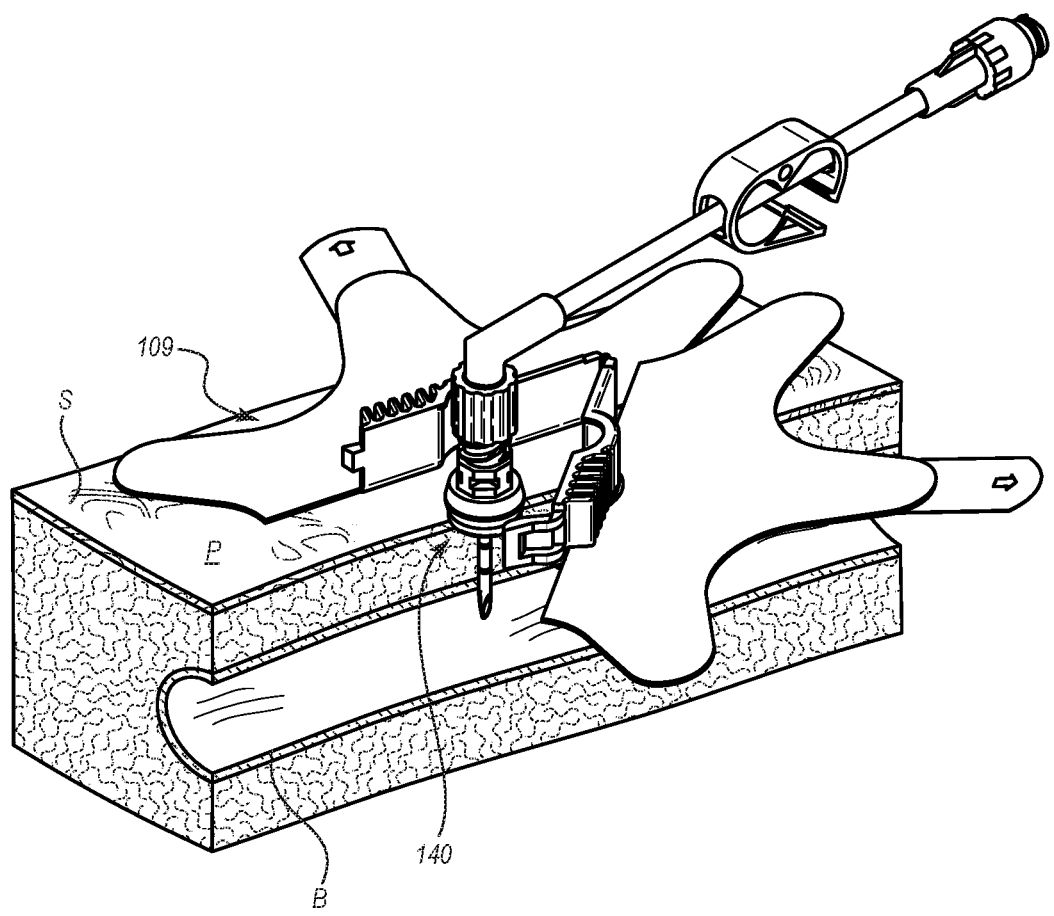
FIG. 14E is a perspective view of a later stage of the illustrative method in which the securement device is placed about the cannula hub while in the open orientation.

FIG. 14E is a perspective view of a later stage of the illustrative method in which the securement device 109 is placed about the needle hub 140 while in the open orientation. The extension assembly 107 can remain coupled to the needle hub 140 without interruption during coupling of the securement device 109 to the needle hub 140.

Figure 14F:
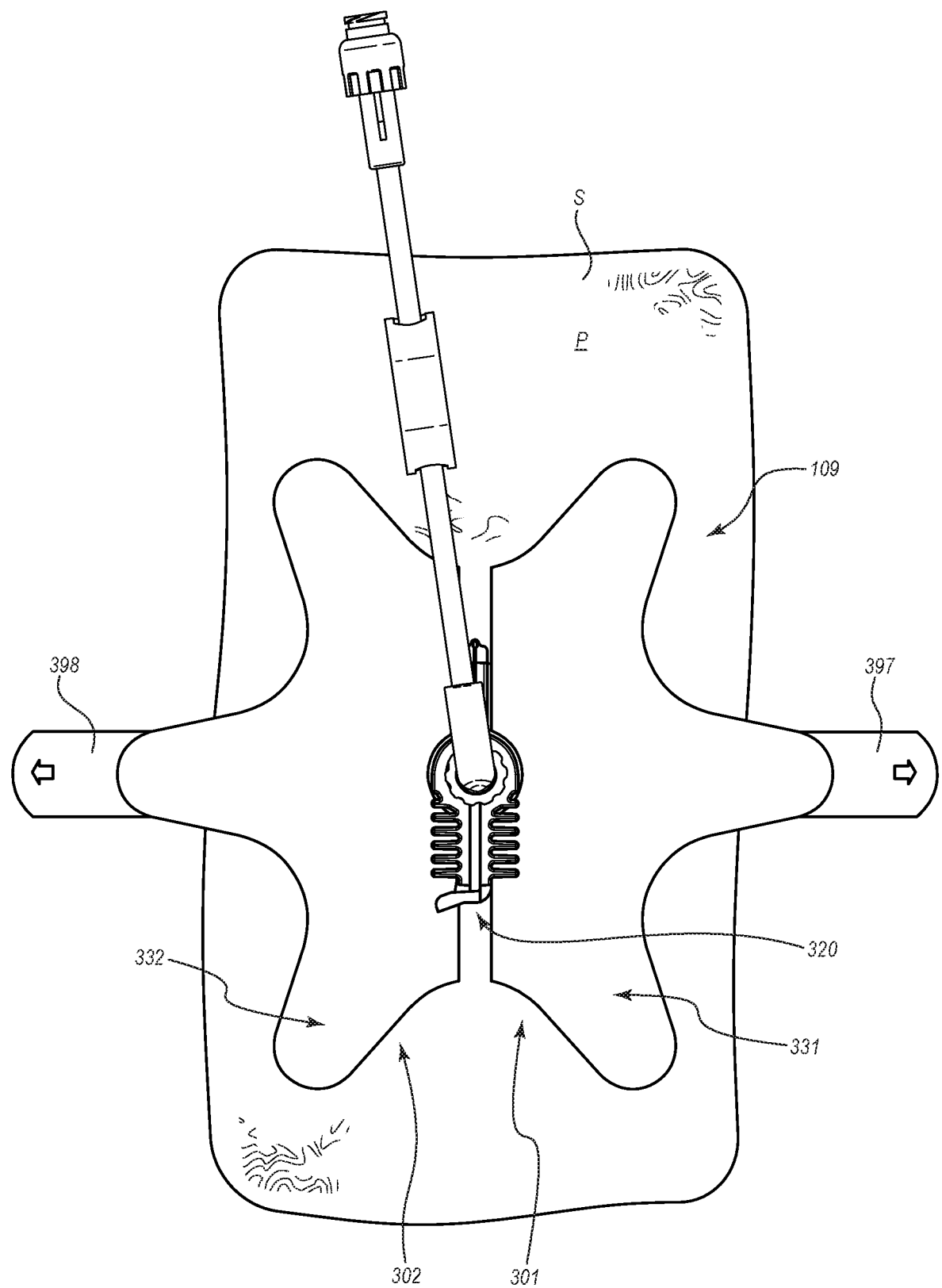
FIG. 14F is a top plan view of a later stage of the illustrative method in which the securement device has been transitioned to a closed orientation about the cannula hub.

FIG. 14F is a top plan view of a later stage of the illustrative method in which the securement device 109 has been transitioned to a closed orientation about the needle hub 140, which is not visible in the illustrated view. The first and second segments 301, 302 of the securement device 109 have been approximated to each other and secured together via the lock 320. In the illustrated embodiment, the first and second dressings 331, 332 move from an overlapping state when the securement device 109 is open, as depicted in FIG. 14E, to a non-overlapping state when the securement device 109 is closed. In the illustrated embodiment, the first and second dressings 331, 332 are spaced from each other, with no portions thereof in an overlapping state, when the securement device 109 is closed.

In the illustrated embodiment, the securement device 109 is being coupled to an arm of the patient P. The pull tabs 397, 398 can be pulled outwardly to expose an adhesive layer of each dressing 331, 332, which adhesive layer can then be pressed against the skin S of the patient to fix the needle hub 140 in place relative to the patient P, or more particularly, relative to an insertion site or access site of the patient P.

Figure 14G:
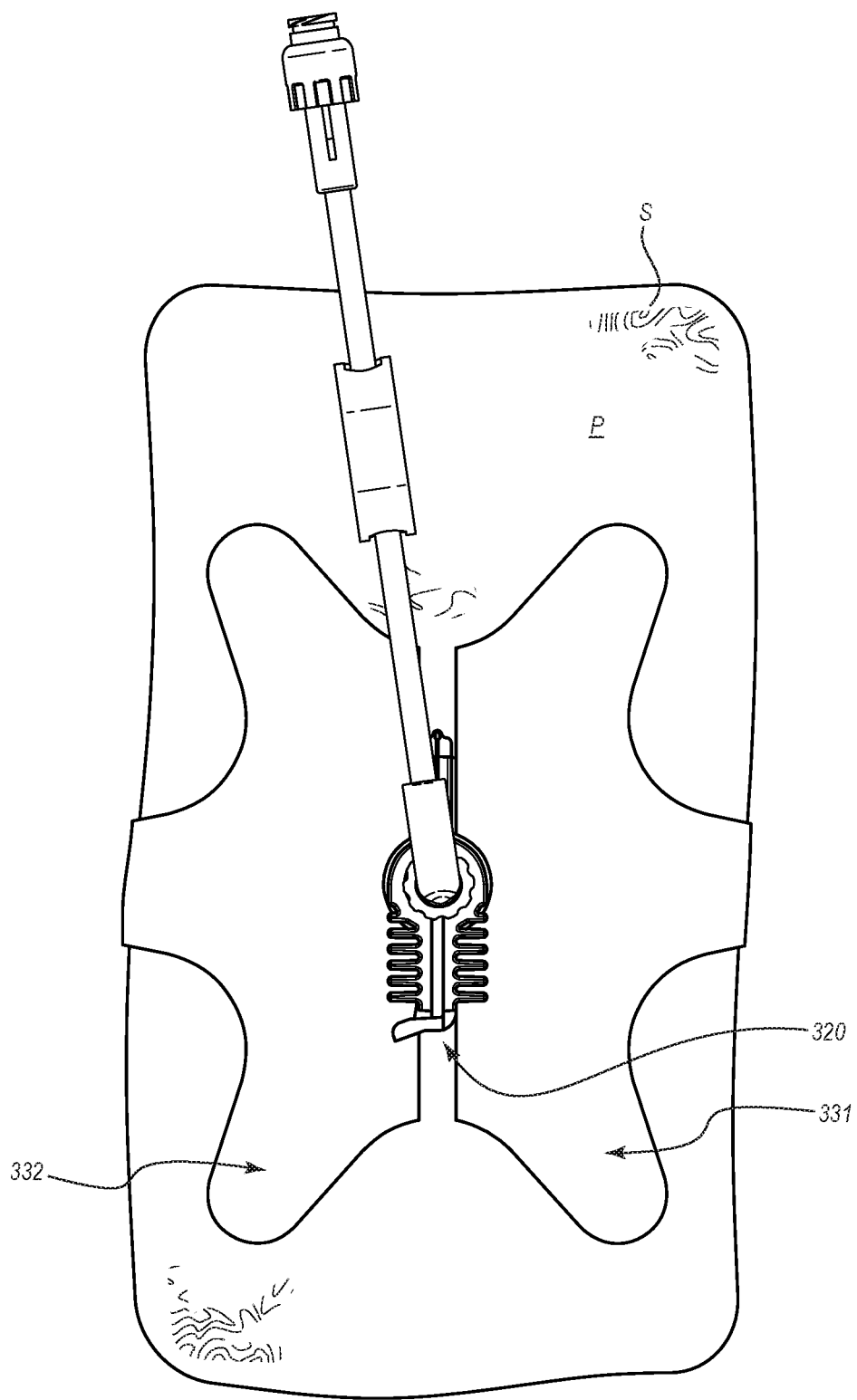
FIG. 14G is a top plan view of a later stage of the illustrative method in which liners have been removed from adhesive dressing portions of the securement device and the adhesive dressings have been adhered to the skin of the patient.

FIG. 14G is a top plan view of a later stage of the illustrative method in which liners 395, 396 (see FIG. 11) have been removed from the dressings 331, 332 and the adhesive layers of the dressings 331, 332 have been pressed to the skin S of the patient P. An arm of each dressing 331, 332 has been wrapped around the arm to achieve a secure attachment and a low profile.

Figure 15:
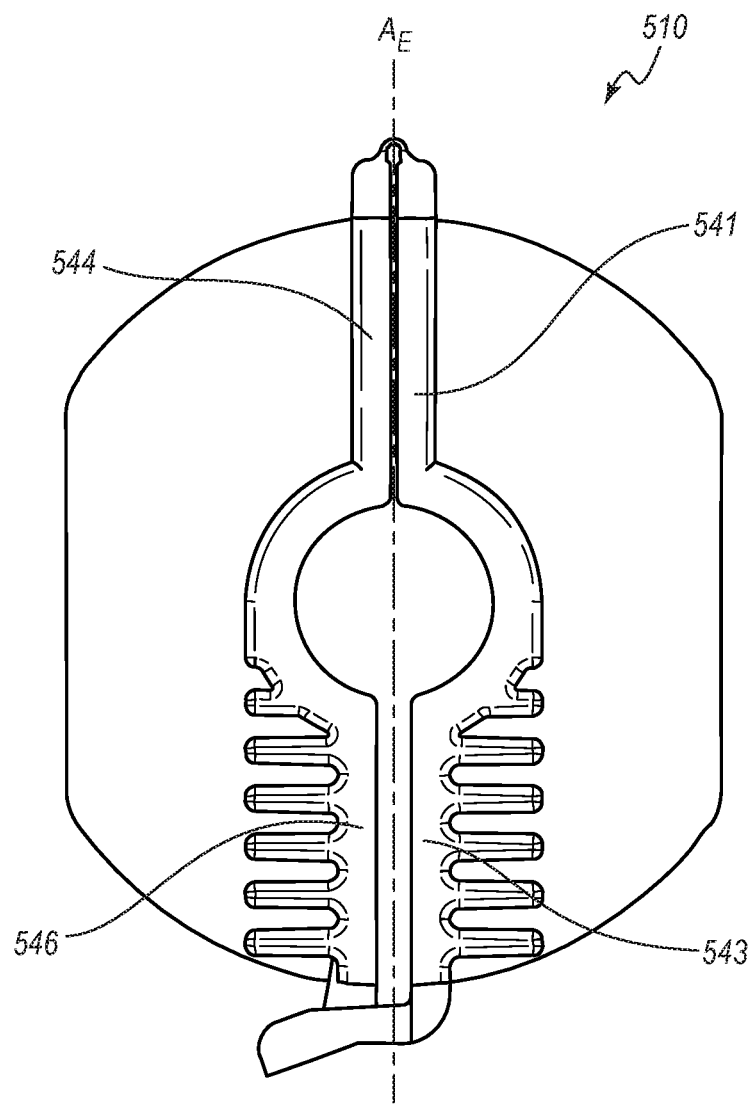
FIG. 15 is a top plan view of another embodiment of a clamp in a closed orientation.

FIG. 15 is a top plan view of another embodiment of a clamp 510 in a closed orientation. The clamp 510 can resemble the clamp 310 described above in certain respects. Accordingly, like features are designated with like reference numerals, with the leading digits incremented to "5." Relevant disclosure set forth above regarding similarly identified features thus may not be repeated hereafter. Moreover, specific features of the clamp 510 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the clamp 510. Any suitable combination of the features and variations of the same described with respect to the clamp 310 can be employed with the clamp 510, and vice versa. This pattern of disclosure applies equally to further embodiments depicted in subsequent figures and described hereafter, wherein the leading digits may be further incremented. Moreover, the clamp 510 may be used with the intraosseous access system 100 or any other suitable system, such as those described elsewhere herein.

The clamp 510 includes outer arms 543, 546 that contact each other along a length thereof when the clamp 510 is in the closed orientation. Stated otherwise, unlike the clamp 310, the clamp 510 does not include a gap between its outer arms 543, 546. Inner faces of the outer arms 543, 546 and a set of inner arms 541, 543 may be aligned along an axis of elongation $A_E$ of the clamp 510.

Figure 16:
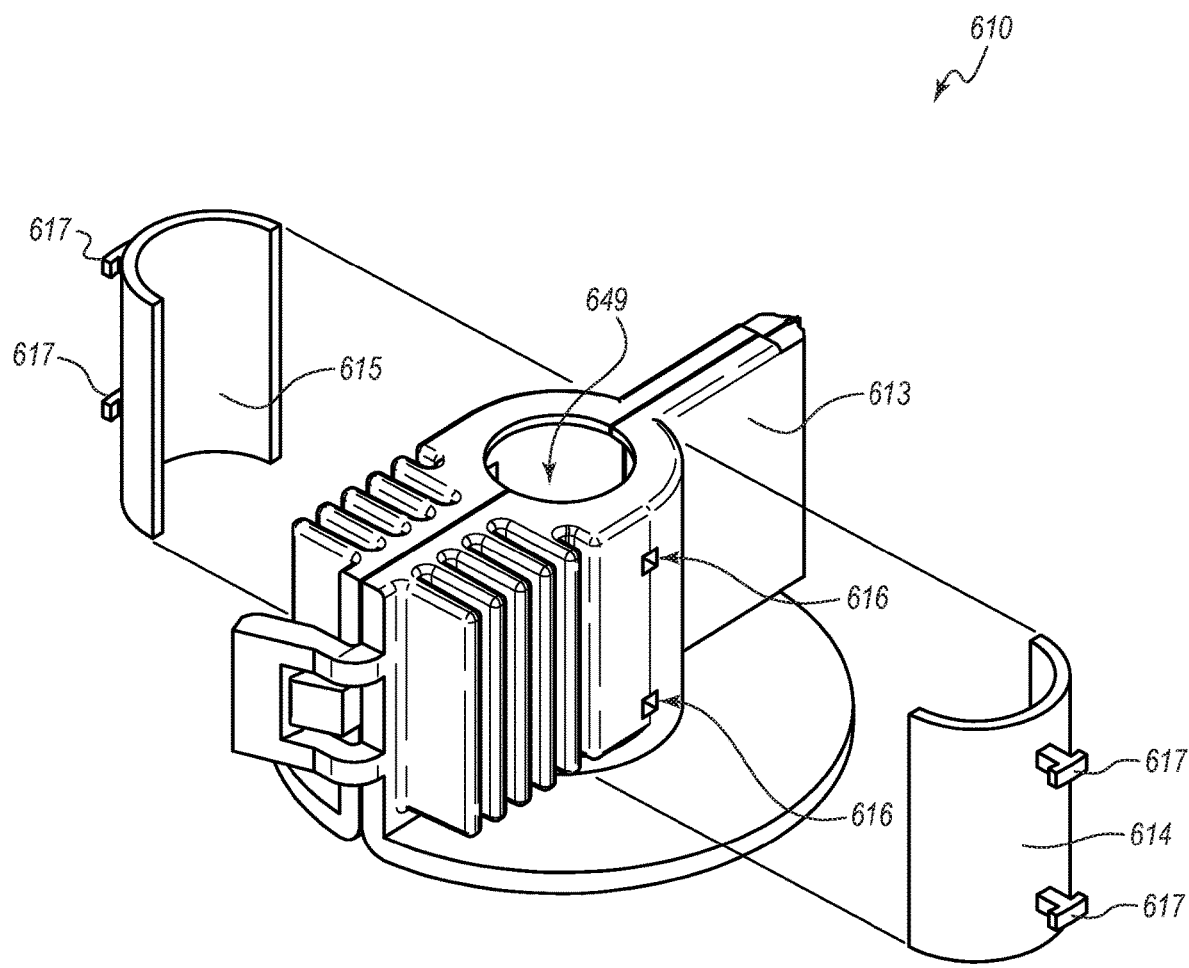
FIG. 16 is an exploded perspective view of another embodiment of a clamp in a closed orientation.

FIG. 16 is an exploded perspective view of another embodiment of a clamp 610 in a closed orientation. The clamp 610 can include a body 613, a first friction-enhancing or gripping insert 614, and a second friction-enhancing or gripping insert 615. The inserts 614, 615 can be positioned within a cavity 649 of the clamp 610, and may be positioned to contact the needle hub 140 when the clamp 610 is secured thereto. The gripping inserts 614, 615 can provide an enhanced frictional engagement with the needle hub 140. The gripping inserts 614, 615 can be formed of any suitable material, such as an elastomeric material (e.g., silicone).

Figure 17:
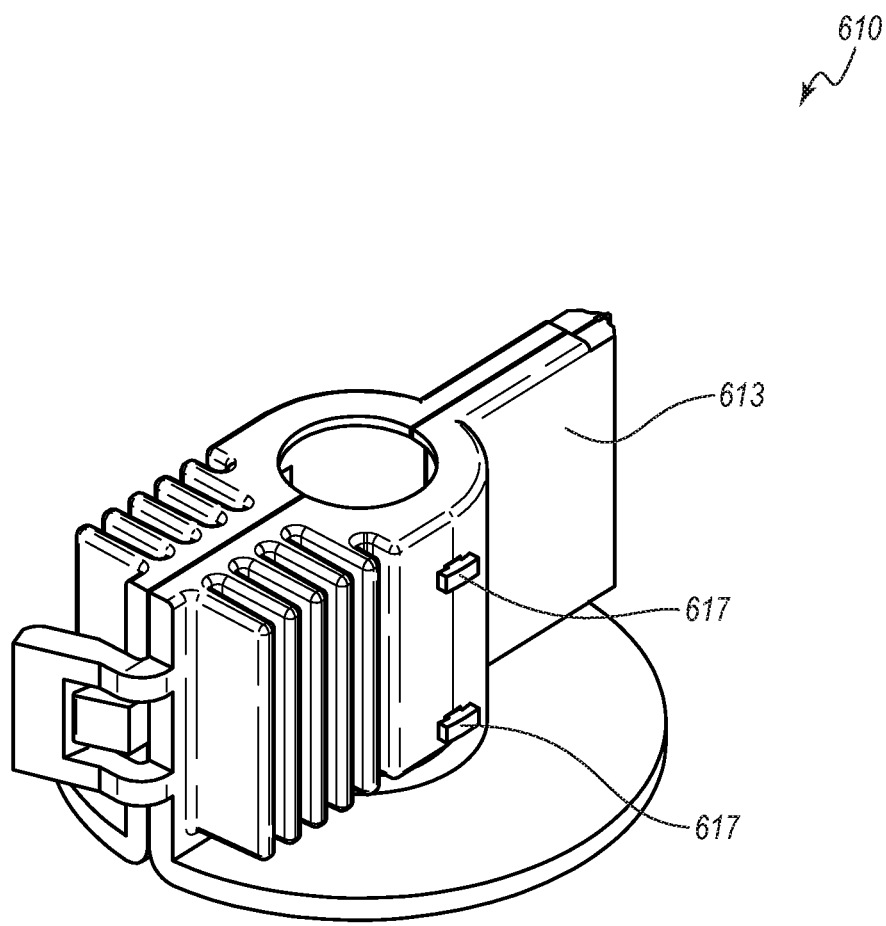
FIG. 17 is another perspective view of the clamp of FIG. 16 in an assembled state.

The inserts 614, 615 may be coupled with the body 613 in any suitable manner. In the illustrated embodiment, the body 613 defines a plurality of openings 616 and the inserts 614, 615 define a plurality of tabs 617 that are configured to pass through the openings 616 in an outward direction and engage an outer surface of the body 613, as shown in FIG. 17.

Figure 18:
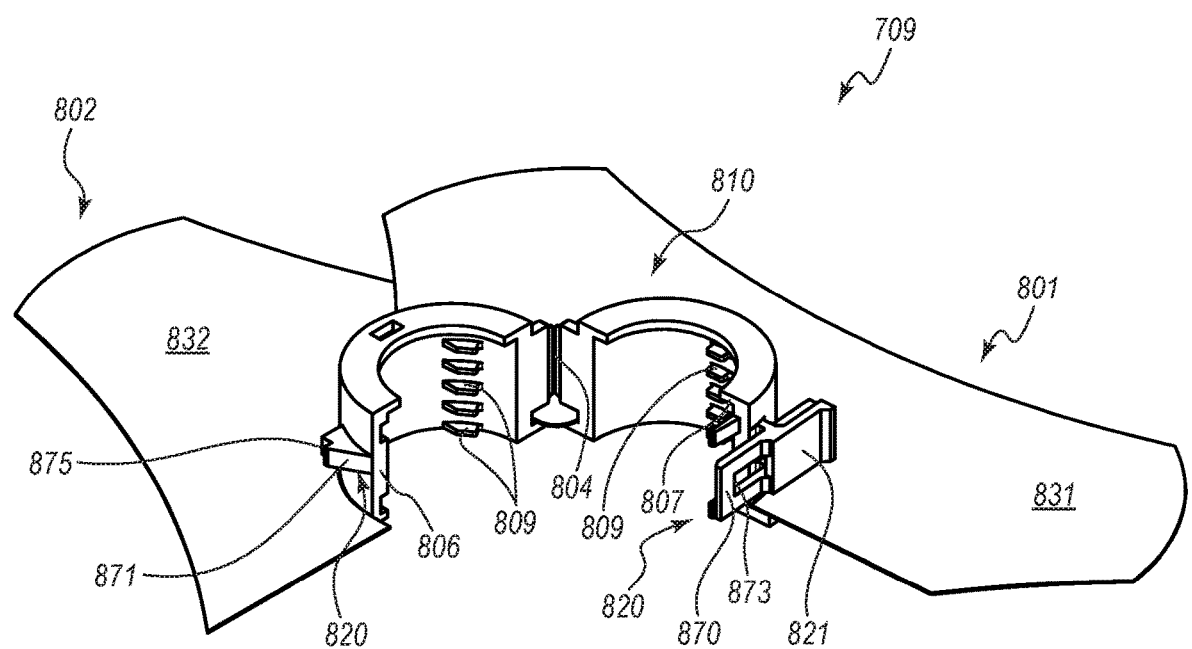
FIG. 18 is a perspective view of another embodiment of a securement device in an open orientation.
Figure 19:
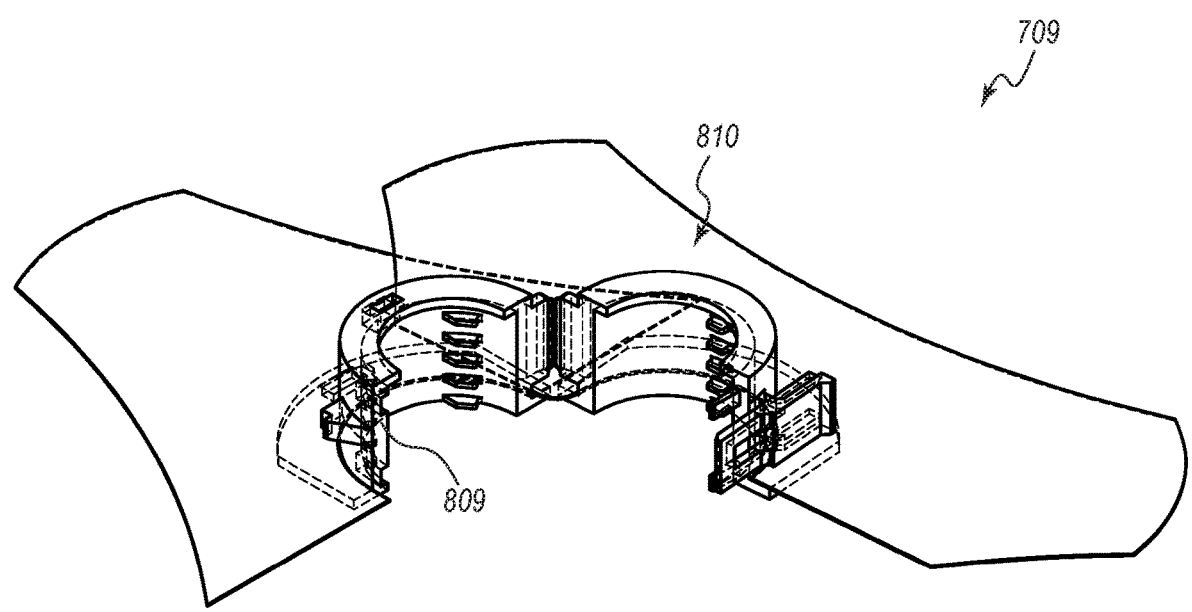
FIG. 19 is another perspective view of the securement device of FIG. 18 in the open state with a clamp portion of the securement device depicted in broken lines.
Figure 20:
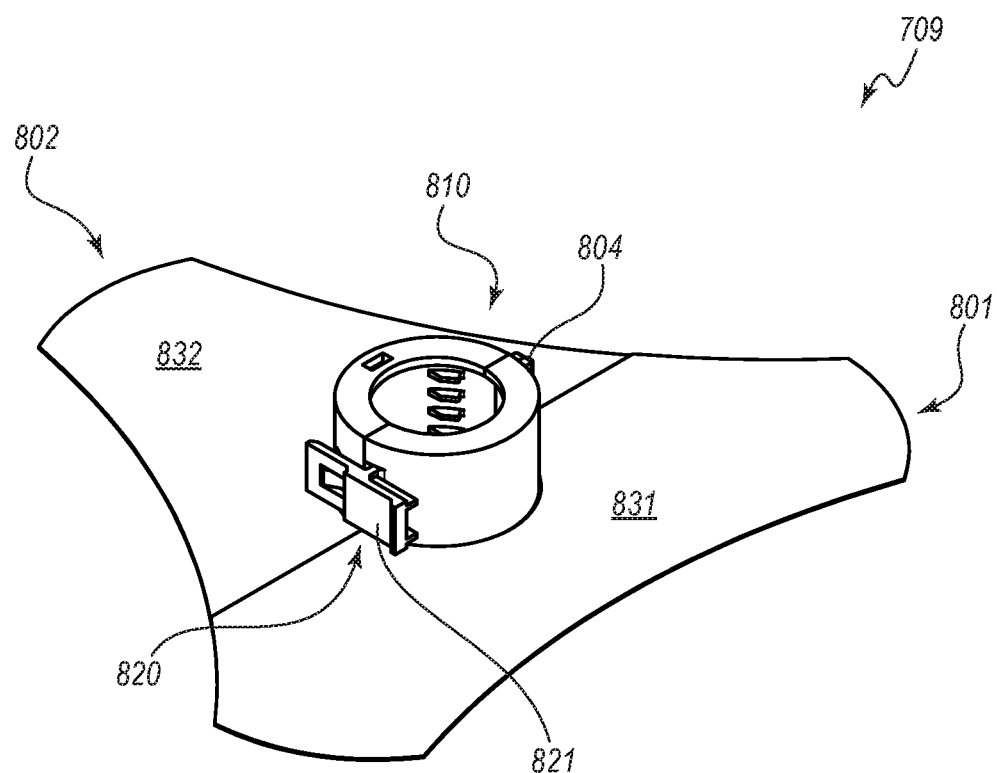
FIG. 20 is a perspective view of the embodiment of the securement device of FIG. 18 in a closed orientation.
Figure 21:
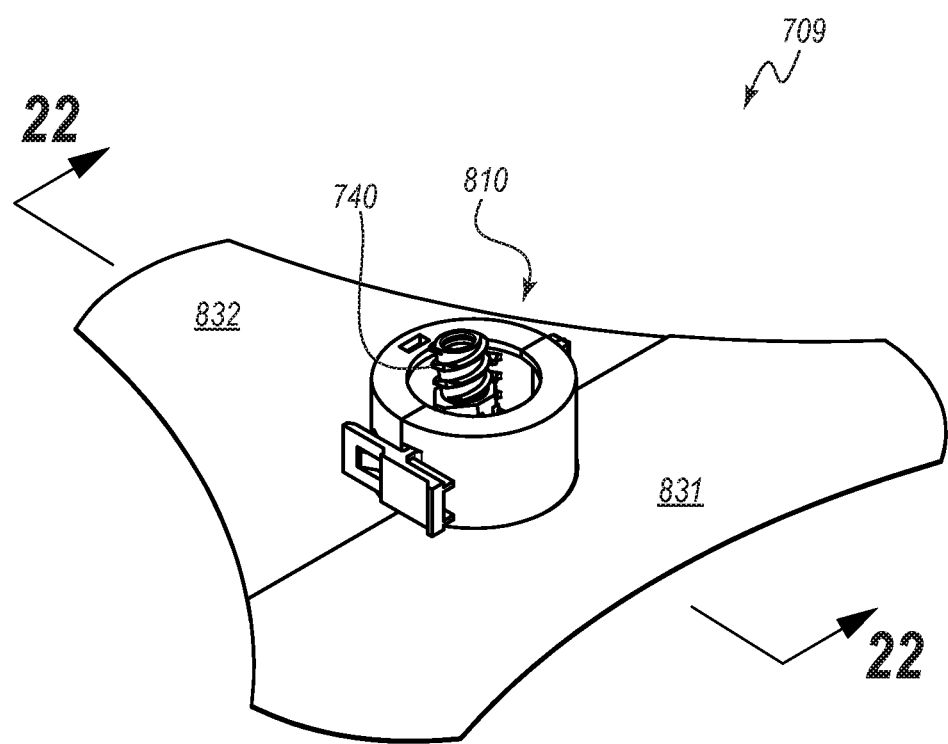
FIG. 21 is a perspective view of the securement device of FIG. 18 in the closed orientation and coupled to a cannula hub.
Figure 22:
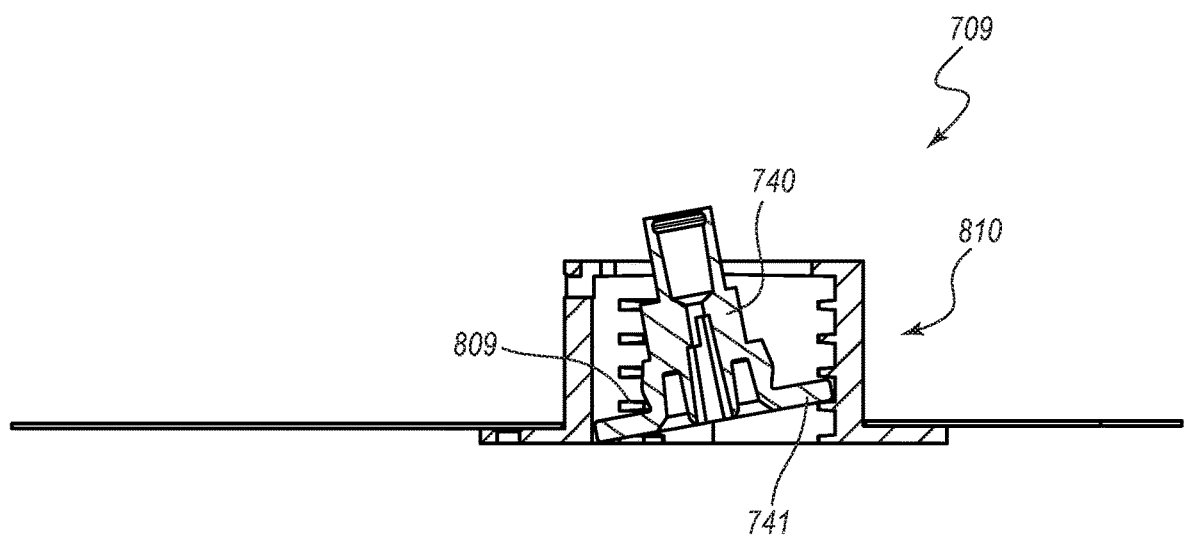
FIG. 22 is a cross-sectional view of the securement device and the cannula hub taken along the view line 22-22 in FIG. 21.
Figure 23:
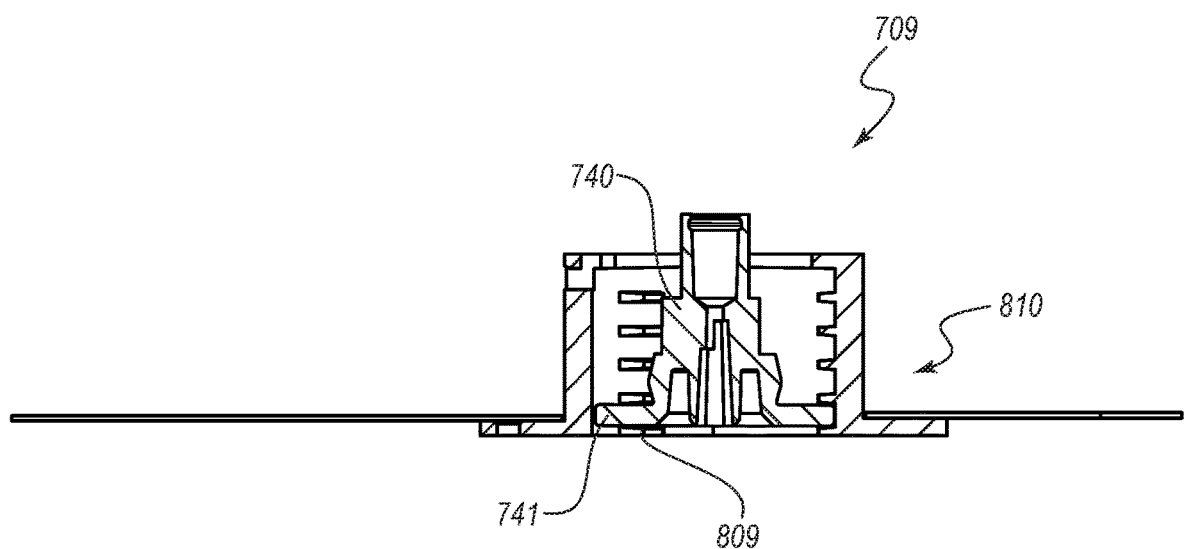
FIG. 23 is a cross-sectional view of the securement device and the cannula hub, such as that of FIG. 22, in which the cannula hub is at a different angle relative to the securement device.

FIGS. 18-23 are various views of another embodiment of a securement device 709 in various phases of operation. FIG. 18 depicts the securement device 709 in an open state or condition. FIG. 19 is another perspective view of the securement device 709 in the open condition with a clamp portion of the securement device depicted in broken lines. FIG. 20 is a perspective view of the securement device 709 in a closed state or condition. FIG. 21 is a perspective view of the securement device 709 the closed orientation and coupled to a needle hub 740. FIG. 22 is a cross-sectional view of the securement device 709 and the needle hub 740 that depicts an off-axis condition of the needle hub 740 with respect to the securement device 709. FIG. 23 is another cross-sectional view of the securement device 709 and the needle hub in which the needle hub 740 is in an on-axis condition relative to the securement device 709.

With continued reference to FIGS. 18-23, the securement device 709 can include a hinge 804 and a lock 820 (e.g., a snap or latch) to capture a needle hub 740 (see FIG. 22) at any of multiple angles. The securement device 709 includes inwardly protruding nubs 809 that allow for capture of a flange or disk portion 741 (see FIG. 22) of the needle hub 740. The nubs 809 are placed and sized such that the needle hub 740 can be placed at any of multiple angles inside of the securement device 709. The securement device 709 can comprise a clamshell configuration, which can permit placement of the securement device 709 after a needle (which is coupled with the needle hub 740) has been placed into a patient. In further instances, the clamshell configuration can permit coupling of the securement device 709 to the needle hub 740 after the needle hub 740 has been attached to a threaded luer connection of an extension tubing or other device for fluid access, such as the extension set 107 (see FIG. 1). As with other embodiments described herein, the securement device 709 can be used to capture the needle hub 740 and secure the same relative to a patient, which can inhibit or prevent accidental dislodgement of the needle hub.

The securement device 709 can include a first segment 801 and a second segment 802 that can be moveable or rotatable relative to each other, when the securement device 709 is in an open condition, and that can be secured to each other to maintain the securement device 709 in a locked or closed condition. The securement device 709 can include a housing or clamp 810 and an adhesive dressing, which can be formed in two sections. In particular, the adhesive dressing includes an adhesive dressing 831 and another adhesive dressing 832. The clamp 810 can include a hinge 804. The clamp 810 can be closed such that a surface 806 thereof substantially makes contact with a surface 807 thereof.

The clamp 810 can be maintained in a closed state by virtue of a locking mechanism or lock 820 that incorporates a latch 870 and a catch 871. Features, or surfaces, of the latch 870 and the catch 871 can engage with each other to maintain the closed configuration. In particular, the latch 870 can include a surface 873 that engages a surface 875 of the catch.

The dressings 831, 832 can be bound to the clamp 810. The dressing can be applied to a body part (e.g., arm, leg) such that the clamp 810 is likewise attached to and substantially fixed relative to the body part.

An interior of the clamp 810 includes a plurality of inwardly protruding projections or nubs 809. In the illustrated embodiment, three sets of nubs 809 are angularly spaced from each other about an interior of the clamp 810. Each set of nubs includes four nubs 809, which are vertically aligned. The sets of nubs are angularly spaced from each other, or are offset, by 120 degrees. Other or further embodiments may have larger or smaller nubs 809, nubs 809 of different geometrical configurations, more or fewer nubs 809, more or fewer nub sets, and/or different spacing of the nub sets.

The illustrated embodiment is particularly well suited for engaging a needle hub 740 that includes an outwardly extending disk or flange 741 (see FIG. 22). A subset of the nubs 809 can engage the flange 741 when the clamp 810 is closed around the hub 740. The allows the securement device 709 to be secured to the hub 740 after the hub 740 has already been secured to a separate access device, and without having to first remove the access device from the hub 740.

In many instances, after the hub 740 has been placed into the body of a patient, it can be desirable to connect an access device to the hub 740 to either aspirate or inject fluid. In some instances, the access device may be connected to the hub 740 via an extension set, such as the extension set 107 discussed above. Moreover, it can be desirable to leave the access device or the extension set in place. In the illustrated embodiment, the securement device 709 can be placed substantially around the hub 740 while the clamp 810 is in the open condition. This allows the aspiration and infusion connection to remain in place. The clamp 801 is then closed around the hub 740 such that the nubs 809 engage the hub flange 741, thus fixing a position of the hub 740 relative to the clamp 810. The dressings 831, 832 can then be applied to the patient's body to substantially fix the securement device 709 to the patient's body.

The clamp 810 can permit the hub 740 to be off-axis, relative to a longitudinal axis of a cavity defined by the clamp 810, in any of a variety of different orientations. The nubs 809 can be of a height, width, and length and/or can be of a spacing relative to adjacent nubs 809 such that the hub flange 741 can be held between vertically adjacent nubs 809. Moreover, the spacing between angularly adjacent nubs may be such as to permit the hub flange 741 to be positioned at an angle relative to a longitudinal axis of the clamp 810. A thickness and/or a diameter of the flange 741 can also factor into the size, shape, and/or orientation of the nubs 809 so as to permit the flange 741 to be held by a subset of the nubs 809 when the hub 740 is in an on-axis orientation and so as also to permit the flange 741 to be held by a different subset of the nubs 809 when the hub 740 is in an off-axis orientation.

In some instances, if the nubs 809 are too small and/or spaced too far apart (e.g., vertically or angularly), the nubs 809 do not securely engage with the hub flange 741. In some instances, if the nubs 809 are too large and/or too close together (e.g., vertically or angularly), the flange 741 is not permitted to enter between the nubs 809 to be engaged thereby and/or is prevented from achieving an angled or off-axis configuration, such as to adapt to a non-planar surface of a patient's skin or anatomy more generally.

The lock 820 can be closed automatically, in manners such as described above. Similarly, the illustrated lock 820 can be selectively disengaged. In particular, in the illustrated embodiment, the lock 820 can be released by applying force to the surface 821 (see FIGS. 18 and 20), which rotates the latch 870 off of the catch 871, or stated otherwise, causes the surfaces 873, 875 to disengage.

In the illustrated embodiment, the clamp 810 is cylindrical and the hub flange 741 is disk shaped or cylindrical. In other embodiments, the clamp 810 can be any of a variety of other shapes or configurations to permit the nubs 809 to engage with the hub flange 741. In still other or further embodiments, the flange 741 may be any shape that would permit the nubs 809 to engage the flange 741 in a variety of orientations. The flange 741 may be continuous, as shown, or discontinuous.

In the illustrated embodiment, the hinge 804 is a living hinge, such as may be manufactured from any suitable plastic. In other embodiments, the hinge 804 may be of any suitable design, and can permit the first and second segments 801, 802 to rotate relative to each other between the open and closed orientations.

The clamp 810 may be manufactured from any suitable material, such as plastic, metal, wood, or other rigid material. The nubs 809 may be formed of the same material or of a different material from other portions of the clamp 810.

Figure 24:
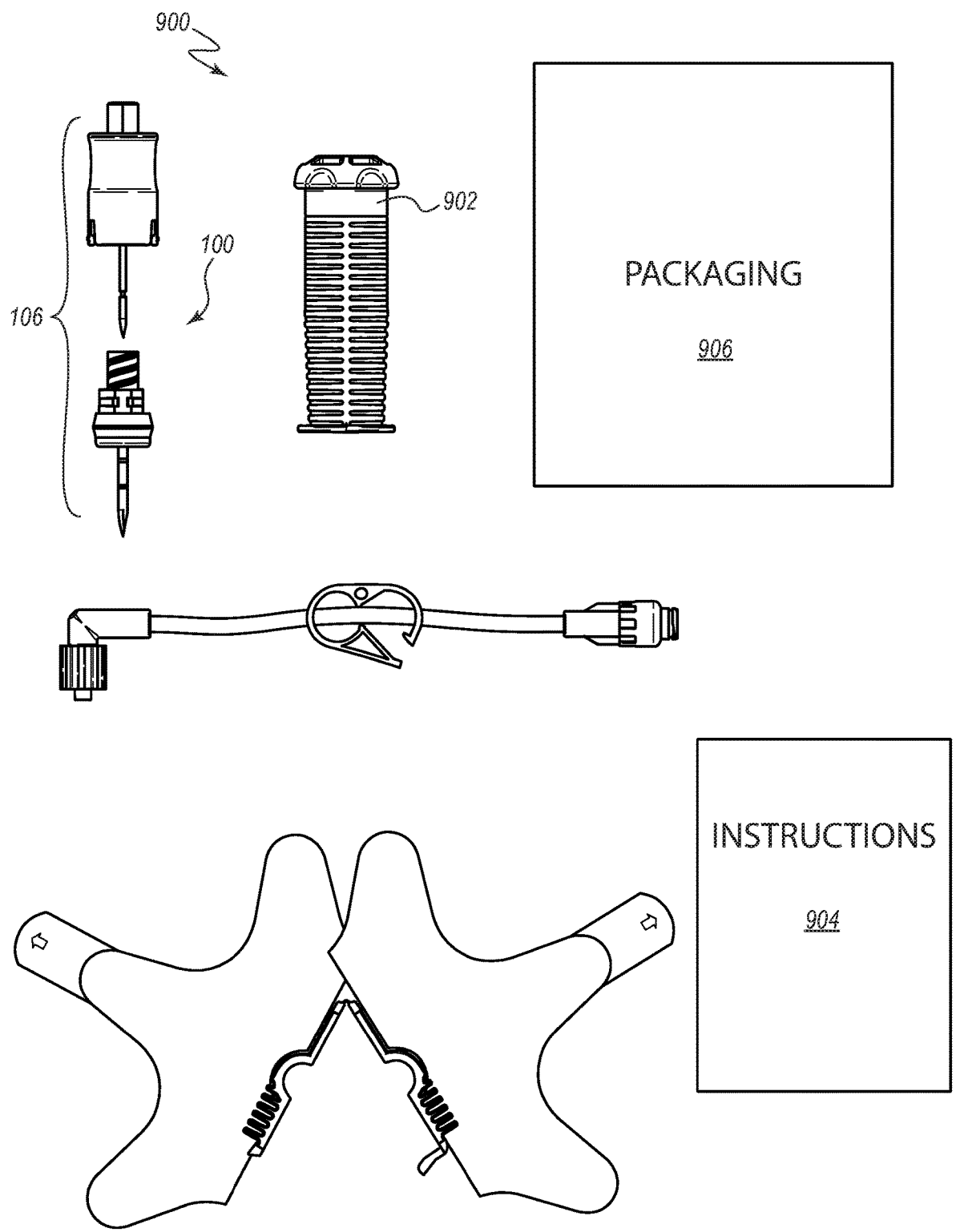
FIG. 24 depicts a kit that includes an embodiment of an intraosseous access system, such as the system depicted in FIG. 1.

FIG. 24 depicts a kit 900 that includes an embodiment of the intraosseous access system 100. The kit 900 can further include a manual driver 902 that can be coupled with the access assembly 106 to achieve fluid communication with the interior of the bone of the patient. Components of the kit 900 can be used in various methods discussed herein.

The kit 900 can include any suitable combination of the components of the intraosseous access system 100. Other components may also be included in the kit 900, such as a sterilization or site preparation pad (not shown) that can be used to prepare an access site prior to inserting the access assembly 106 into the patient. In some embodiments, the kit 900 includes instructions 904. The instructions 904 can include directions for performing any and/or all of the steps of a method for achieving access to an interior of a bone, such as any of the procedures discussed above. For example, in some embodiments, the instructions 904 are instructions for use for the access system 100. In other or further embodiments, the instructions 904 may provide directions for accessing such directions. For example, the instructions may list a web address, a mailing address, and/or a telephone number that can be used to locate instructions for using the access system 100. One or more of the foregoing items can be included in and/or on (e.g., in the case of the instructions) any suitable packaging 906.

The term "patient" is used broadly herein and is not intended to be limiting. A patient can be, for example, any individual who undergoes any of the methods or treatments discussed herein, whether in a hospital, first responder, or other setting. The term "patient" includes humans, mammals, or any other animal possessing anatomy compatible with embodiments described herein.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth.

It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to"

each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:
1. A system comprising:
a hub;
a cannula coupled to the hub, the cannula comprising a distal end configured to be introduced into a bone of a patient to provide fluid communication between an interior of the bone and the hub;

a securement device configured to couple with the hub when transitioned from an open orientation to a closed orientation, the securement device comprising:
  a first segment and a second segment that are configured to be spaced apart from each other when the securement device is in the open orientation and are configured to be approximated and secured to each other when the securement device is in the closed orientation,
  the first segment comprising:
    a first receptacle configured to receive a portion of the hub therein and contact the hub to restrain movement of the hub relative to the securement device when the securement device is coupled with the hub in the closed orientation; and
    a first arm coupled to the first receptacle, the first arm being configured to bias the first receptacle toward the hub when the securement device is coupled with the hub in the closed orientation; and
  a clamp that defines at least a portion of each of the first and second segments, the clamp comprising a hinge about which the first and second segments rotate as the securement device is transitioned from the open orientation to the closed orientation.

2. The system of claim 1, wherein the first arm is configured to be in a flexed state when the securement device is in the closed orientation.

3. The system of claim 2, wherein the first arm is configured to remain in the flexed state while the securement device is in the closed orientation to continuously bias the first receptacle toward the hub.

4. The system of claim 1, wherein at least a portion of the first arm is configured to transition from a relaxed state when the securement device is in the open orientation to a deformed state as the securement device is transitioned to the closed orientation.

5. The system of claim 4, wherein said at least a portion of the first arm is configured to remain in the deformed state while the securement device is in the closed orientation to continuously bias the first receptacle toward the hub.

6. The system of claim 1, wherein the second segment comprises:
  a second receptacle configured to receive a portion of the hub therein and contact the hub to restrain movement of the hub relative to the securement device when the securement device is coupled with the hub in the closed orientation; and
  a second arm coupled to the second receptacle, the second arm being configured to bias the second receptacle toward the hub when the securement device is coupled with the hub in the closed orientation.

7. The system of claim 6, wherein the second arm is configured to be in a flexed state when the securement device is in the closed orientation.

8. The system of claim 7, wherein the second arm is configured to remain in the flexed state while the securement device is in the closed orientation to continuously bias the second receptacle toward the hub.

9. The system of claim 6, wherein the securement device comprises a lock configured to maintain the securement device in the closed orientation, wherein the first arm extends between the first receptacle and the lock, and wherein the second arm extends between the second receptacle and the lock.

10. The system of claim 9, wherein the securement device further comprises a hinge about which the first and second segments rotate relative to each other when the securement device transitions from the open orientation to the closed orientation.

11. The system of claim 10, wherein the hinge and the lock are at opposite sides of the hub when the securement device is coupled with the hub.

12. The system of claim 1, wherein the first arm extends away from the first receptacle at an exterior thereof.

13. The system of claim 1, wherein the first arm is not in contact with the hub when the securement device is coupled with the hub in the closed orientation.

14. The system of claim 1, wherein the hinge defines an axis of rotation, wherein the clamp defines an axis of elongation that is substantially orthogonal to the axis of rotation, and wherein the first arm is elongated in a direction that is substantially collinear with or substantially parallel to the axis of elongation when the securement device is in the open orientation.

15. The system of claim 1, wherein the clamp further comprises a lock via which the first and second segments are secured to each other.

16. The system of claim 15, wherein the lock and the hinge are positioned at opposite ends of the clamp.

17. The system of claim 1, wherein the securement device comprises an adhesive dressing that is configured to attach the securement device to the skin of the patient.

18. A system comprising:
  a hub;
  a cannula coupled to the hub, the cannula comprising a distal end configured to be introduced into a bone of a patient to provide fluid communication between an interior of the bone and the hub; and
  a clamp configured to transition from an open orientation to a closed orientation, the clamp comprising:
    an elongated first branch that comprises a first end, a second end, and a receptacle spaced from the first and second ends;
    an elongated second branch that comprises a first end and a second end; and
    a hinge coupled to the first end of the elongated first branch and to the first end of the elongated second branch,
    wherein the elongated first branch transitions from a relaxed state to a flexed state when the clamp is transitioned to the closed orientation with at least a portion of the hub being positioned between the elongated first branch and the elongated second branch and being positioned in the receptacle of the elongated first branch, and
    wherein the elongated first branch remains in the flexed state while the clamp is maintained in the closed orientation.

19. A system comprising:
  a hub;
  a cannula coupled to the hub, the cannula comprising a distal end configured to be introduced into a bone of a patient to provide fluid communication between an interior of the bone and the hub; and
  a clamp configured to transition from an open orientation to a closed orientation, the clamp comprising:
    an elongated first branch that comprises a first end and a second end;
    an elongated second branch that comprises a first end and a second end;
    a hinge coupled to the first end of the elongated first branch and to the first end of the elongated second branch; and a lock coupled to the second end of the elongated first branch and to the second end of the elongated second branch, wherein each of the elongated first branch and the elongated second branch transitions from a relaxed state to a flexed state when the clamp is transitioned to the closed orientation with at least a portion of the hub being positioned between the elongated first branch and the elongated second branch, and wherein when the lock is secured with said at least a portion of the hub positioned between the elongated first branch and the elongated second branch, each of the elongated first branch and the elongated second branch remains in the flexed state.

20. A system comprising:

a hub;

a cannula coupled to the hub, the cannula comprising a distal end configured to be introduced into a bone of a patient to provide fluid communication between an interior of the bone and the hub;

a securement device configured to couple with the hub when transitioned from an open orientation to a closed orientation, the securement device comprising a first segment and a second segment that are configured to be spaced apart from each other when the securement device is in the open orientation and are configured to be approximated and secured to each other when the securement device is in the closed orientation, the first segment comprising:
    a first receptacle configured to receive a portion of the hub therein and contact the hub to restrain movement of the hub relative to the securement device when the securement device is coupled with the hub in the closed orientation; and
    a first arm coupled to the first receptacle, the first arm being configured to bias the first receptacle toward the hub when the securement device is coupled with the hub in the closed orientation; and the second segment comprising:
    a second receptacle configured to receive a portion of the hub therein and contact the hub to restrain movement of the hub relative to the securement device when the securement device is coupled with the hub in the closed orientation; and
    a second arm coupled to the second receptacle, the second arm being configured to bias the second receptacle toward the hub when the securement device is coupled with the hub in the closed orientation.

21. The system of claim 20, wherein the second arm is configured to be in a flexed state when the securement device is in the closed orientation.

22. The system of claim 21, wherein the second arm is configured to remain in the flexed state while the securement device is in the closed orientation to continuously bias the second receptacle toward the hub.

23. The system of claim 20, wherein the securement device comprises a lock configured to maintain the securement device in the closed orientation, wherein the first arm extends between the first receptacle and the lock, and wherein the second arm extends between the second receptacle and the lock.

24. The system of claim 23, wherein the securement device further comprises a hinge about which the first and second segments rotate relative to each other when the securement device transitions from the open orientation to the closed orientation.

25. The system of claim 24, wherein the hinge and the lock are at opposite sides of the hub when the securement device is coupled with the hub.

\* \* \* \* \*